United States Patent
Edelberg et al.

(10) Patent No.: US 7,504,379 B2
(45) Date of Patent: Mar. 17, 2009

(54) PROTECTION OF CARDIAC MYOCARDIUM

(75) Inventors: Jay Edelberg, New York, NY (US); Munira Xaymardan, Toronto (CA)

(73) Assignee: Cornell Research Foundation, Inc., Ithaca, NY (US)

( * ) Notice: Subject to any disclaimer, the term of this patent is extended or adjusted under 35 U.S.C. 154(b) by 233 days.

(21) Appl. No.: 11/129,076

(22) Filed: May 13, 2005

(65) Prior Publication Data
US 2006/0019891 A1   Jan. 26, 2006

Related U.S. Application Data

(63) Continuation-in-part of application No. PCT/US03/36644, filed on Nov. 14, 2003.

(60) Provisional application No. 60/426,124, filed on Nov. 14, 2002.

(51) Int. Cl.
A61K 38/18 (2006.01)
A61K 38/19 (2006.01)

(52) U.S. Cl. .......................... 514/12; 514/2

(58) Field of Classification Search ............... None
See application file for complete search history.

(56) References Cited

U.S. PATENT DOCUMENTS

| | | | |
|---|---|---|---|
| 3,561,444 A | 2/1971 | Boucher | |
| 3,703,173 A | 11/1972 | Dixon | |
| 4,051,842 A | 10/1977 | Hazel et al. | |
| 4,140,122 A | 2/1979 | Kuhl et al. | |
| 4,383,529 A | 5/1983 | Webster | |
| 4,624,251 A | 11/1986 | Miller | |
| 4,635,627 A | 1/1987 | Gam et al. | |
| 4,962,091 A | 10/1990 | Eppstein et al. | |
| 5,149,792 A | 9/1992 | Thomason | |
| 6,331,302 B1 | 12/2001 | Bennett et al. | |
| 6,541,008 B1 * | 4/2003 | Wise et al. | 424/198.1 |
| 6,676,937 B1 | 1/2004 | Isner et al. | |
| 6,748,258 B1 * | 6/2004 | Mueller et al. | 600/425 |
| 2003/0228659 A1 | 12/2003 | Ballinger et al. | |

FOREIGN PATENT DOCUMENTS

| | | |
|---|---|---|
| WO | WO 88/07057 * | 9/1988 |
| WO | WO-94/07529 A1 | 4/1994 |
| WO | WO-94/10202 A1 | 5/1994 |
| WO | WO-96/11269 A2 | 4/1996 |
| WO | WO-96/31598 A1 | 10/1996 |
| WO | WO-01/05825 A2 | 1/2001 |
| WO | WO-2004/045531 A2 | 6/2004 |

OTHER PUBLICATIONS

Henry, TD. BMJ. 1999; 318: 1536-1539.*
Herren et al. Biochim Biophys Acta. 1993 25; 1173(3):294-302.*
Encyclopædia Britannica. 2008. Encyclopædia Britannica Online. Oct. 2008; downloaded on Jan. 10, 2007 at britannica.com/eb/article-45351; 2 pages.*
Cheng et al. Pharmaceutical Research, 2006; 23: 557-564.*
"International Search Report for corresponding PCT Application No. PCT/US03/36644", (Feb. 3, 2005), 2 pgs.
Aird, W., "Vascular Bed-Specific Expression of an Endothelial Cell Gene Is Programmed by the Tissue Microenvironment", *The Journal of Cell Biology*, 138(5), (1997), 1117-1124.
Ataliotis, P., "Distribution and Functions of Platelet-Derived Growth Factors and Their Receptors During Embryogenesis", *International Review of Cytology*, 172, (1997), 95-127.
Betsholtz, C., "Role of Platelet-Derived Growth Factors in Mouse Development", *Int. J. Dev. Biol.*, 39(5), (Oct. 1995), 817-825.
Blanc-Brude, O. P., et al., "Inhibitor of Apoptosis Protein Survivin Regulates Vascular Injury", *Nature Medicine*, 8(9), (Sep. 2002), 987-994.
Breier, G., "Functions of the VEGF/VEGF Receptor System in the Vascular System", *Seminars in Thrombosis and Hemostasis*, 26(5), (2000), 553-559.
Brooks, P. C., et al., "Requirement of Vascular Integrin $\alpha_v\beta_3$ for Angiogenesis", *Science*, 264(5158), (Apr. 22, 1994), 569-571.
Cai, D., et al., "Age-Associated Impairment in TNF-α Cardioprotection From Myocardial Infarction", *American Journal of Physiology—Heart and Circulatory Physiology*, 285, (2003), H463-H469.
Cheng, W., et al., "Programmed Myocyte Cell Death Affects the Viable Myocardium After infarction in Rats", *Experimental Cell Research*, 226, (1996), 316-327.
Christini, D. J., "Direct Biologically Based Biosensing of Dynamic Physiological Function", *American Journal of Physiology—Heart and Circulatory Physiology*, 280, (2001),H2006-H2010.
Davis, T. A., et al., "Ex Vivo Expansion of Primitive Murine Hematopoietic Progenitor Cells on Porcine Endothelial Cells", *Transplantation Proceedings*, 29, (1997), p. 2005.
Davis, S., et al., "Isolation of Angiopoietin 1, a Ligand for the TIE2 Receptor, by Secretion-Trap Expression Cloning", *Cell*, 87, (Dec. 27, 1996),1161-1169.
De Vries, C., et al., "The *fms*-Like Tyrosine Kinase, a Receptor for Vascular Endothelial Growth Factor", *Science*, 255(5047), (Feb. 21, 1992), 989-991.
Dellian, M., et al., "Quantitation and Physiological Characterization of Angiogenic Vessels in Mice: Effect of Basic Fibroblast Growth Factor, Vascular Endothelial Growth Factor/Vascular Permeability Factor, and Host Microenvironment", *The American Journal of Pathology*, 149(1), (1996), 59-71.
Deuel, T., "Human Platelet-Derived Growth Factor", *The Journal of Biological Chemistry*, 256(17), (Sep. 10, 1981), 8896-8899.
Edelberg, J. M., "Enhanced Myocyte-Based Biosensing of the Blood-Borne Signals Regulating Chronotropy", *Journal of Applied Physiology*, 92(2), (Feb. 2002), 581-585.

(Continued)

*Primary Examiner*—Elizabeth C. Kemmerer
*Assistant Examiner*—Christina Borgeest
(74) *Attorney, Agent, or Firm*—Schwegman, Lundberg & Woessner, P.A.

(57) ABSTRACT

The invention provides compositions and methods for protecting vascular tissues from injury that occurs, for example, during occlusion of one or more arteries. In some embodiments, the injury is myocardial infarction. The compositions of the invention include combinations of platelet derived growth factor, vascular endothelial growth factor, and angiopoietin-2.

32 Claims, 13 Drawing Sheets

OTHER PUBLICATIONS

Edelberg, J., "PDGF Mediates Cardiac Microvascular Communication", *Journal of Clinical Investigation*, 102(4), (1998),837-843.

Edelberg, J., "Platelet-Derived Growth Factor-AB Limits the Extent of Myocardial infarction in a Rat Model: Feasibility of Restoring Impaired Angiogenic Capacity in the Aging Heart", *Circulation*, 105(5), (Feb. 5, 2002), 608-613.

Edelberg, J., "Young Adult Bone Marrow-Derived Endothelial Precursor Cells Restore Aging-Impaired Cardiac Angiogenic Function", *Circulation Research*, 90(10), (May 31, 2002), e89-e93.

Ferrara, N., et al., "Molecular and Biological Properties of the Vascular Endothelial Growth Factor Family of Proteins", *Endocrine Reviews*, 13(1), (1992), 18-32.

Finnerty, H., et al., "Molecular Cloning of Murine FLT and FLT4", *Oncogene*, 8(8), (1993), 2293-2298.

Galland, F., et al., "The FLT4 Gene Encodes a Transmembrane Tyrosine Kinase Related to the Vascular Endothelial Growth Factor Receptor", *Oncogene*, 8(5), (1993), 1233-1240.

Gottlieb, R. A., et al., "Apoptosis in Myocardial Ischemia-Reperfusion", *Annals of New York Academy of Sciences*, 874, (1999), 412-426.

Guttenplan, N., et al., "Inhibition of Myocardial Apoptosis as a Therapeutic Target in Cardiovascular Disease Prevention: Focus on Caspase Inhibition", *Heart Disease*, 3(5), (2001), 313-318.

Hakuno, D., et al., "Bone Marrow-Derived Regenerated Cardiomyocytes (CMG Cells) Express Functional Adrenergic and Muscarinic Receptors", *Circulation*, 105(3), (Jan. 22, 2002), 380-386.

Heldin, C.-H., "Chemical and Biological Properties of a Growth Factor From Human -Cultured Osteosarcoma Cells: Resemblance With Platelet-Derived Growth Factor", *Journal of Cellular Physiology*, 105, (1980), 235-246.

Hillebrands, J.-L., et al., "Origin of Neointimal Endothelium and α-actin-positive Smooth Muscle Cells in Transplant Arteriosclerosis", *The Journal of Clinical Investigation*, 107(11), (2001), 1411-1422.

Hinescu, M. E., "Cardiac Apoptosis: From Organ Failure to Allograft Rejection", *J. Cell. Mol. Med.*, 5(2), (2001), 143-152.

Holash, J., et al., "Vessel Cooption, Regression, and Growth in Tumors Mediated by Angiopoietins and VEGF", *Science*, 284(5422), (Jun. 18, 1999), 1994-1998.

Jackson, K. A., "Regeneration of Ischemic Cardiac Muscle and Vascular Endothelium By Adult Stem Cells", *The Journal of Clinical Investigation*, 107(11), (Jun. 2001), 1395-1402.

Katada, J., et al., "Significance of Vascular Endothelial Cell Growth Factor Up-Regulation Mediated via a Chymase-Angiotensin-Dependent Pathway During Angiogenesis in Hamster Sponge Granulomas", *The Journal of Pharmacology and Experimental Therapeutics*, 302(3), (2002), 949-956.

Kim, I., et al., "Angiopoietin-2 at High Concentration Can Enchance Endothelial Cell Survival Through the Phosphatidylinositol 3'-kinase/Akt Signal Transduction Pathway", *Oncogene*, 19, (2000), 4549-4552.

Kovacs, P., et al., "Non-Specific Caspase Inhibition Reduces Infrarct Size and Improves Post-Ischaemic Recovery in Isolated Ischaemic/Reperfused Rat Hearts", *Naunyn-Schmiedeberg's Arch Pharmacol.*, 364, (2001), 501-507.

Liu, W., et al., "Antiangiogenic Therapy Targeting Factors That Enhance Endothelial Cell Survival", *Seminars in Oncology*, 29(3, Suppl 11), (Jun. 2002), 96-103.

Makino, S., "Cardiomyocytes Can Be Generated From Marrow Stromal Cells in vitro", *The Journal of Clinical Investigation*, 103(5), (1999), 697-705.

Malouf, N., et al., "Adult-Derived Stem Cells From the Liver Become Myocytes in the Heart in Vivo", *American Journal of Pathology*, 158(6), (2001), 1929-1935.

Matthews, W., et al., "A Receptor Tyrosine Kinase cDNA Isolated From a Population of Enriched Primitive Hematopoietic Cells and Exhibiting Close Genetic Linkage to c-kit", *Proc. Natl. Acad. Sci. USA*, 88, (Oct. 1991), 9026-9030.

Millauer, B., et al., "High Affinity VEGF Binding and Developmental Expression Suggest Flk-1 as a Major Regulator of Vasculogenesis and Angiogenesis", *Cell*, 72(6), (Mar. 26, 1993), 835-846.

Möhle, R., "Expression of Interleukin-5 by Human Bone Marrow Microvascular Endothelial Cells: Implications for the Regulation of Eosinophilopoiesis in vivo", *British Journal of Haematology*, 99, (1997), 732-738.

Mustonen, T., et al, "Endothelial Receptor Tyrosine Kinases Involved in Angiogenesis", *The Journal of Cell Biology*, 129(4), (1995), 895-898.

Oelrichs, R. B., et al., *NYK/FLK-1*: A Putative Receptor Protein Tyrosine Kinase Isolated From E10 Embryonic Neuroepithelium is Expressed in Endothelial Cells of the Developing Embryo, *Oncogene*, 8(1), (1993), 11-18.

Orlic, D., et al., "Bone Marrow Cells Regenerate Infarcted Myocardium", *Nature*, 410, (Apr. 5, 2001), 701-705.

Pajusola, K., et al., "FLT4 Receptor Tyrosine Kinase Contains Seven Immunoglobulin-Like Loops and Is Expressed in Multiple Human Tissues and Cell Lines", *Cancer Research*, 52(20), (Oct. 15, 1992), 5738-5743.

Palmer, T., "Vascular Niche for Adult Hippocampal Neurogenesis", *The Journal of Comparative Neurology*, 425, (2000), 479-494.

Patan, S., "Vasculogenesis and Angiogenesis as Mechanisms of Vascular Network Formation, Growth and Remodeling", *Journal of Neuro-Oncology*, 50(1-2), (2000), 1-15.

Quinn, T. P., et al., "Fetal Liver Kinase 1 is a Receptor for Vascular Endothelial Growth Factor and is Selectively Expressed in Vascular Endothelium", *Proc. Natl. Acad. Sci. USA*, 90, (Aug. 1993), 7533-7537.

Rafii, S., "Human Bone Marrow Microvascular Endothelial Cells Support Long-Term Proliferation and Differentiation of Myeloid and Megakaryocytic Progenitors", *Blood*, 86(9), (1995), 3353-3363.

Rafii, S., "Regulation of Hematopoiesis by Microvascular Endothelium", *Leukemia & Lymphoma*, 27, (1997), 375-386.

Raines, E. W., "Platelet-Derived Growth Factor. I. High Yield Purification and Evidence for Multiple Forms.", *The Journal of Biological Chemistry*, 257(9), (May, 10, 1982), 5154-5160.

Ray, P. S., et al., "Early Effects of Hypoxia/Reoxygenation on VEGF, Ang-1, Ang-2 and Their Receptors in the Rat Myocardium: Implications for Myocardial Angiogenesis", *Molecular and Cellular Biochemistry*, 213, (2000), 145-153.

Richardson, T. P., et al., "Polymeric System of Dual Growth Factor Delivery", *Nature Biotechnology*, 19, (2001), 1029-1034.

Shibuya, M., "Nucleotide Sequence and Expression of a Novel Human Receptor-Type Tyrosine Kinase Gene (*flt*) Closely Related to the *fms* Family", *Oncogene*, 5(4), (1990), 519-524.

Springer, M. L., et al., "Not the Usual Suspects: The Unexpected Sources of Tissue Regeneration", *The Journal of Clinical Investigation*, 107(11), (2001), 1355-1356.

Sullivan, L. W., "Healthy People 2000", *The New England Journal of Medicine*, 323(15), (Oct. 11, 1990), 1065-1067.

Terman, B. I., et al., "Identification of a New Endothelial Cell Growth Factor Receptor Tyrosine Kinase", *Oncogene*, 6(9), (1991), 1677-1683.

Terman, B. I., et al., "Identification of the KDR Tyrosine Kinase as a Receptor for Vascular Endothelial Cell Growth Factor", *Biochemical and Biophysical Research Communications*, 187(3), (Sep. 30, 1992), 1579-1586.

Tomei, L. D., et al., "Apoptosis and the Heart—A Brief Review", *Annals New York Academy of Sciences*, 946, (2001), 160-168.

Umansky, S. R. et al., "Apoptosis in the Heart", *Advances in Pharmacology*, 41, (1997), 383-407.

Wang, T., et al., "Differential Expression of Nitric Oxide Synthases in EGF-Responsive Mouse Neural Precursor Cells", *Cell Tissue Research*, 296, (1999),489-497.

Wei, J. Y., "Age and the Cardiovascular System", *The New England Journal of Medicine*, 327(24), (Dec. 10, 1992), 1735-1739.

Weinsaft, J., "Aging-Associated Changes in Vascular Activity: A Potential Link To Geriatric Cardiovascular Disease", *The American Journal of Geriatric Cardiology*, 10(6), (2001), 348-354.

Xue, L., et al., "Angiogenic Effect of Fibroblast Growth Factor-1 and Vascular Endothelial Growth Factor and Their Synergism in a Novel in Vitro Quantitative Fibrin-Based 3-Dimensional Angiogenesis System", *Surgery*, 132, (2002), 259-267.

Yoshiji, H., et al., "Synergistic Effect of Basic Fibroblast Growth Factor and Vascular Endothelial Growth Factor in Murine Hepatocellular Carcinoma", *Hepatology*, 35 (4), (2002), 834-842.

Yourey, P., "Vascular Endothelial Cell Growth Factors Promote the In Vitro Development of Rat Photoreceptor Cells", *The Journal of Neuroscience*, 20(18), (2000), 6781-6788.

Zou, Z., et al., "*dl*-3-Hydroxybutyrate Administration Prevents Myocardial Damage After Coronary Occlusion in Rat Hearts", *American Journal of Physiology—Heart and Circulatory Physiology*, 283, (2002), H1968-H1974.

\* cited by examiner

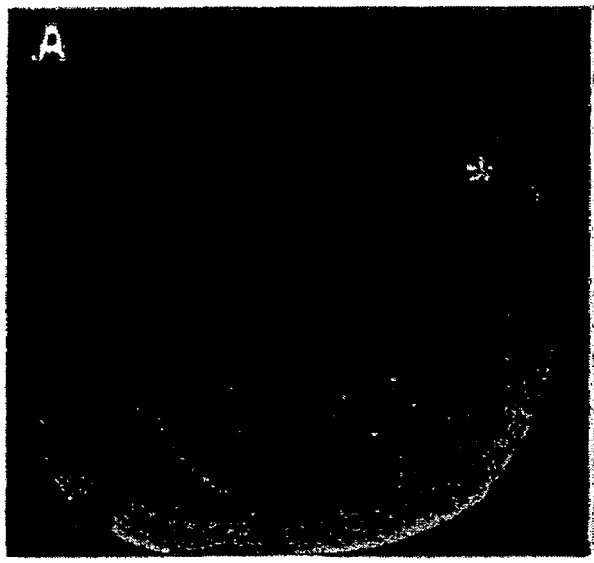 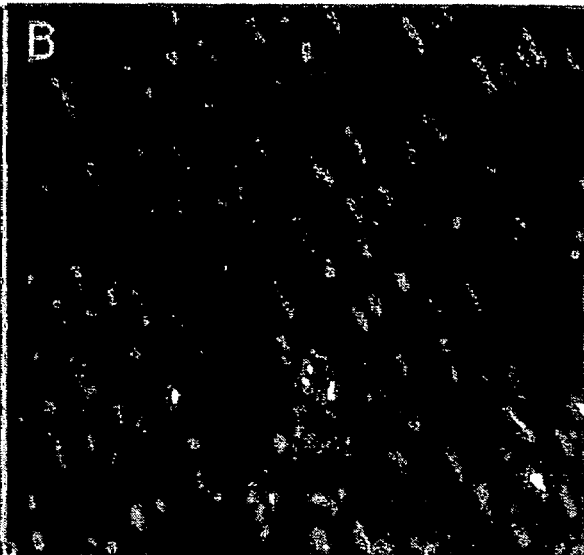
FIG. 4A  FIG. 4B
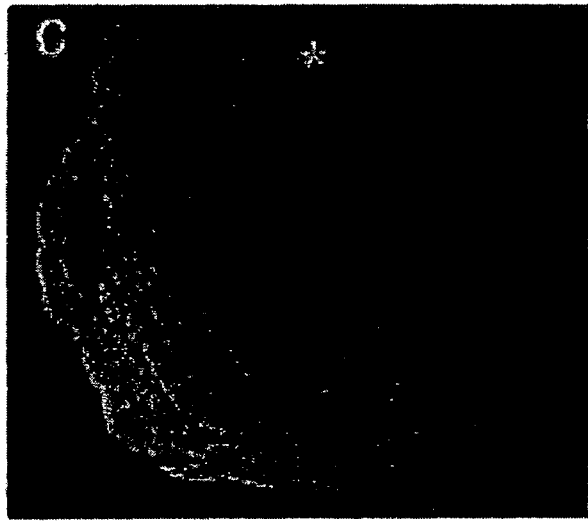 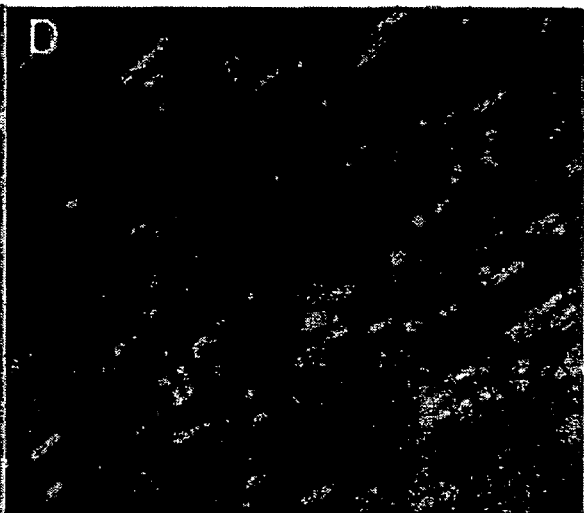
FIG. 4C  FIG. 4D

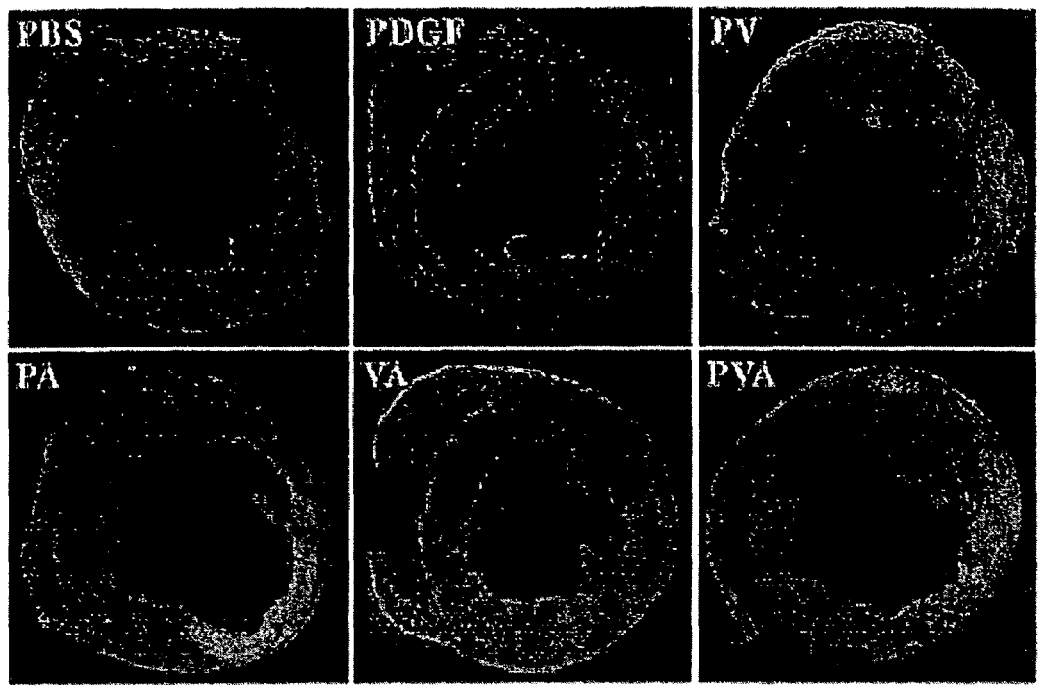
FIG. 9A
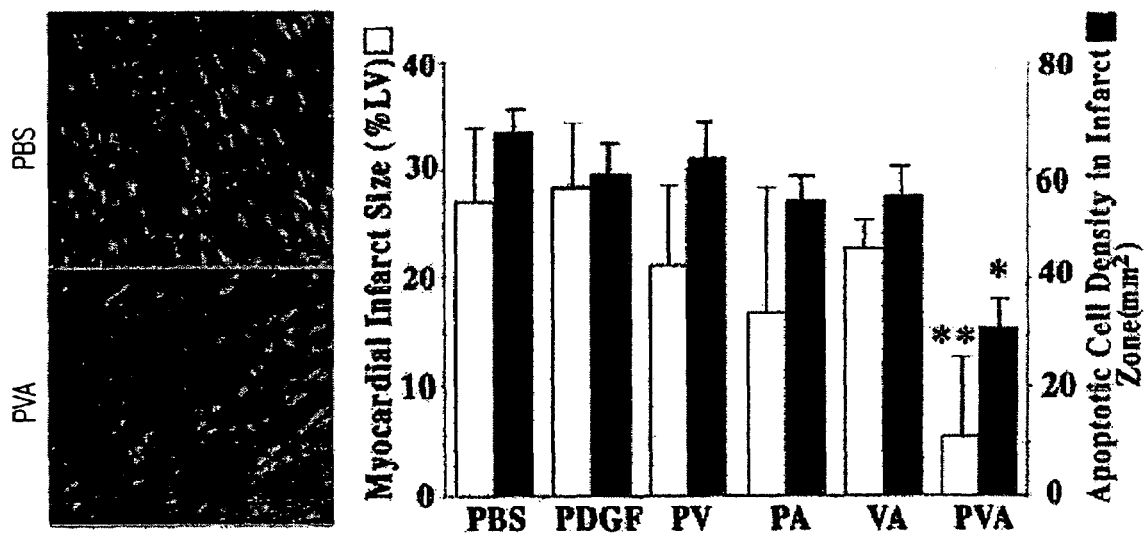
FIG. 9B
FIG. 9C

SEQUENCE LISTING

```
<160> NUMBER OF SEQ ID NOS: 18

<210> SEQ ID NO 1
<211> LENGTH: 204
<212> TYPE: PRT
<213> ORGANISM: Homo sapiens

<400> SEQUENCE: 1

Met Arg Thr Trp Ala Cys Leu Leu Leu Gly Cys Gly Tyr Leu Ala
1               5                   10                  15

His Ala Leu Ala Glu Glu Ala Glu Ile Pro Arg Glu Leu Ile Glu Arg
                20                  25                  30

Leu Ala Arg Ser Gln Ile His Ser Ile Arg Asp Leu Gln Arg Leu Leu
            35                  40                  45

Glu Ile Asp Ser Val Gly Ala Glu Asp Ala Leu Glu Thr Asn Leu Arg
        50                  55                  60

Ala His Gly Ser His Thr Val Lys His Val Pro Glu Lys Arg Pro Val
65                  70                  75                  80

Pro Ile Arg Arg Lys Arg Ser Ile Glu Glu Ala Ile Pro Ala Val Cys
                85                  90                  95

Lys Thr Arg Thr Val Ile Tyr Glu Ile Pro Arg Ser Gln Val Asp Pro
                100                 105                 110

Thr Ser Ala Asn Phe Leu Ile Trp Pro Pro Cys Val Glu Val Lys Arg
            115                 120                 125

Cys Thr Gly Cys Cys Asn Thr Ser Ser Val Lys Cys Gln Pro Ser Arg
        130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu His Leu Glu
                165                 170                 175

Cys Ala Cys Ala Thr Ser Asn Leu Asn Pro Asp His Arg Glu Glu Glu
            180                 185                 190

Thr Gly Arg Arg Arg Glu Ser Gly Lys Lys Arg Lys
        195                 200

<210> SEQ ID NO 2
<211> LENGTH: 196
<212> TYPE: PRT
<213> ORGANISM: Mus musculus

<400> SEQUENCE: 2

Met Arg Thr Trp Ala Cys Leu Leu Leu Gly Cys Gly Tyr Leu Ala
1               5                   10                  15

His Ala Leu Ala Glu Glu Ala Glu Ile Pro Arg Glu Leu Ile Glu Arg
                20                  25                  30

Leu Ala Arg Ser Gln Ile His Ser Ile Arg Asp Leu Gln Arg Leu Leu
            35                  40                  45

Glu Ile Asp Ser Val Gly Ala Glu Asp Ala Leu Glu Thr Ser Leu Arg
        50                  55                  60
```

```
Ala His Gly Ser His Ala Ile Asn His Val Pro Glu Lys Arg Pro Val
 65                  70                  75                  80

Pro Ile Arg Arg Lys Arg Ser Ile Glu Glu Ala Val Pro Ala Val Cys
                 85                  90                  95

Lys Thr Arg Thr Val Ile Tyr Glu Ile Pro Arg Ser Gln Val Asp Pro
            100                 105                 110

Thr Ser Ala Asn Phe Leu Ile Trp Pro Pro Cys Val Glu Val Lys Arg
        115                 120                 125

Cys Thr Gly Cys Cys Asn Thr Ser Ser Val Lys Cys Gln Pro Ser Arg
    130                 135                 140

Val His His Arg Ser Val Lys Val Ala Lys Val Glu Tyr Val Arg Lys
145                 150                 155                 160

Lys Pro Lys Leu Lys Glu Val Gln Val Arg Leu Glu Glu Asp Leu Glu
                165                 170                 175

Cys Ala Cys Ala Thr Ser Asn Leu Asn Pro Asp His Arg Glu Glu Glu
            180                 185                 190

Thr Asp Val Arg
        195

<210> SEQ ID NO 3
<211> LENGTH: 241
<212> TYPE: PRT
<213> ORGANISM: Homo sapiens

<400> SEQUENCE: 3

Met Asn Arg Cys Trp Ala Leu Phe Leu Ser Leu Cys Cys Tyr Leu Arg
  1               5                  10                  15

Leu Val Ser Ala Glu Gly Asp Pro Ile Pro Glu Glu Leu Tyr Glu Met
             20                  25                  30

Leu Ser Asp His Ser Ile Arg Ser Phe Asp Asp Leu Gln Arg Leu Leu
         35                  40                  45

His Gly Asp Pro Gly Glu Glu Asp Gly Ala Glu Leu Asp Leu Asn Met
     50                  55                  60

Thr Arg Ser His Ser Gly Gly Glu Leu Glu Ser Leu Ala Arg Gly Arg
 65                  70                  75                  80

Arg Ser Leu Gly Ser Leu Thr Ile Ala Glu Pro Ala Met Ile Ala Glu
                 85                  90                  95

Cys Lys Thr Arg Thr Glu Val Phe Glu Ile Ser Arg Arg Leu Ile Asp
            100                 105                 110

Arg Thr Asn Ala Asn Phe Leu Val Trp Pro Pro Cys Val Glu Val Gln
        115                 120                 125

Arg Cys Ser Gly Cys Cys Asn Asn Arg Asn Val Gln Cys Arg Pro Thr
    130                 135                 140

Gln Val Gln Leu Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Val Ala Ala Ala Arg Pro Val Thr Arg Ser
            180                 185                 190

Pro Gly Gly Ser Gln Glu Gln Arg Ala Lys Thr Pro Gln Thr Arg Val
        195                 200                 205

Thr Ile Arg Thr Val Arg Val Arg Arg Pro Pro Lys Gly Lys His Arg
    210                 215                 220
```

```
Lys Phe Lys His Thr His Asp Lys Thr Ala Leu Lys Glu Thr Leu Gly
225                 230                 235                 240

Ala
```

```
<210> SEQ ID NO 4
<211> LENGTH: 241
<212> TYPE: PRT
<213> ORGANISM: Mus musculus

<400> SEQUENCE: 4
```

```
Met Asn Arg Cys Trp Ala Leu Phe Leu Pro Leu Cys Cys Tyr Leu Arg
 1               5                  10                  15

Leu Val Ser Ala Glu Gly Asp Pro Ile Pro Glu Leu Tyr Glu Met
             20                  25                  30

Leu Ser Asp His Ser Ile Arg Ser Phe Asp Asp Leu Gln Arg Leu Leu
         35                  40                  45

His Arg Asp Ser Val Asp Glu Asp Gly Ala Glu Leu Asp Leu Asn Met
 50                  55                  60

Thr Arg Ala His Ser Gly Val Glu Leu Glu Ser Ser Arg Gly Arg
 65                  70                  75                  80

Arg Ser Leu Gly Ser Leu Ala Ala Ala Glu Pro Ala Val Ile Ala Glu
                 85                  90                  95

Cys Lys Thr Arg Thr Glu Val Phe Gln Ile Ser Arg Asn Leu Ile Asp
            100                 105                 110

Arg Thr Asn Ala Asn Phe Leu Val Trp Pro Pro Cys Val Glu Val Gln
        115                 120                 125

Arg Cys Ser Gly Cys Cys Asn Asn Arg Asn Val Gln Cys Arg Ala Ser
    130                 135                 140

Gln Val Gln Met Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Ile Val Thr Pro Arg Pro Val Thr Arg Ser
            180                 185                 190

Pro Gly Thr Ser Arg Glu Gln Arg Ala Lys Thr Pro Gln Ala Arg Val
        195                 200                 205

Thr Ile Arg Thr Val Arg Ile Arg Arg Pro Pro Lys Gly Lys His Arg
    210                 215                 220

Lys Phe Lys His Thr His Asp Lys Ala Ala Leu Lys Glu Thr Leu Gly
225                 230                 235                 240

Ala
```

```
<210> SEQ ID NO 5
<211> LENGTH: 161
<212> TYPE: PRT
<213> ORGANISM: Homo sapiens

<400> SEQUENCE: 5
```

```
Arg Ser Leu Gly Ser Leu Thr Ile Ala Glu Pro Ala Met Ile Ala Glu
 1               5                  10                  15

Cys Lys Thr Arg Thr Glu Val Phe Glu Ile Ser Arg Arg Leu Ile Asp
             20                  25                  30

Arg Thr Asn Ala Asn Phe Leu Val Trp Pro Pro Cys Val Glu Val Gln
         35                  40                  45

Arg Cys Ser Gly Cys Cys Asn Asn Arg Asn Val Gln Cys Arg Pro Thr
     50                  55                  60
```

Gln Val Gln Leu Arg Pro Val Gln Val Arg Lys Ile Glu Ile Val Arg
65                  70                  75                  80

Lys Lys Pro Ile Phe Lys Lys Ala Thr Val Thr Leu Glu Asp His Leu
                85                  90                  95

Ala Cys Lys Cys Glu Thr Val Ala Ala Ala Arg Pro Val Thr Arg Ser
            100                 105                 110

Pro Gly Gly Ser Gln Glu Gln Arg Ala Lys Thr Pro Gln Thr Arg Val
            115                 120                 125

Thr Ile Arg Thr Val Arg Val Arg Arg Pro Pro Lys Gly Lys His Arg
        130                 135                 140

Lys Phe Lys His Thr His Asp Lys Thr Ala Leu Lys Glu Thr Leu Gly
145                 150                 155                 160

Ala

<210> SEQ ID NO 6
<211> LENGTH: 119
<212> TYPE: PRT
<213> ORGANISM: Homo sapiens

<400> SEQUENCE: 6

Met Asn Arg Cys Trp Ala Leu Phe Leu Ser Leu Cys Cys Tyr Leu Arg
1               5                   10                  15

Leu Val Ser Ala Glu Gly Asp Pro Ile Pro Glu Glu Leu Tyr Glu Met
                20                  25                  30

Leu Ser Asp His Ser Ile Arg Ser Phe Asp Asp Leu Gln Arg Leu Leu
            35                  40                  45

His Gly Asp Pro Gly Glu Glu Asp Gly Ala Glu Leu Asp Leu Asn Met
        50                  55                  60

Thr Arg Ser His Ser Gly Gly Glu Leu Glu Ser Leu Ala Arg Gly Arg
65                  70                  75                  80

Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
            100                 105                 110

Arg Thr Asn Ala Asn Phe Leu
        115

<210> SEQ ID NO 7
<211> LENGTH: 496
<212> TYPE: PRT
<213> ORGANISM: Homo sapiens

<400> SEQUENCE: 7

Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
                20                  25                  30

Gln Tyr Gln Val Gln His Gly Ser Cys Ser Tyr Thr Phe Leu Leu Pro
            35                  40                  45

Glu Met Asp Asn Cys Arg Ser Ser Ser Pro Tyr Val Ser Asn Ala
        50                  55                  60

Val Gln Arg Asp Ala Pro Leu Glu Tyr Asp Asp Ser Val Gln Arg Leu
65                  70                  75                  80

Gln Val Leu Glu Asn Ile Met Glu Asn Asn Thr Gln Trp Leu Met Lys
                85                  90                  95

-continued

```
Leu Glu Asn Tyr Ile Gln Asp Asn Met Lys Lys Glu Met Val Glu Ile
                100                 105                 110
Gln Gln Asn Ala Val Gln Asn Gln Thr Ala Val Met Ile Glu Ile Gly
            115                 120                 125
Thr Asn Leu Leu Asn Gln Thr Ala Glu Gln Thr Arg Lys Leu Thr Asp
        130                 135                 140
Val Glu Ala Gln Val Leu Asn Gln Thr Thr Arg Leu Glu Leu Gln Leu
145                 150                 155                 160
Leu Glu His Ser Leu Ser Thr Asn Lys Leu Glu Lys Gln Ile Leu Asp
                165                 170                 175
Gln Thr Ser Glu Ile Asn Lys Leu Gln Asp Lys Asn Ser Phe Leu Glu
            180                 185                 190
Lys Lys Val Leu Ala Met Glu Asp Lys His Ile Ile Gln Leu Gln Ser
        195                 200                 205
Ile Lys Glu Glu Lys Asp Gln Leu Gln Val Leu Val Ser Lys Gln Asn
210                 215                 220
Ser Ile Ile Glu Glu Leu Glu Lys Lys Ile Val Thr Ala Thr Val Asn
225                 230                 235                 240
Asn Ser Val Leu Gln Lys Gln Gln His Asp Leu Met Glu Thr Val Asn
                245                 250                 255
Asn Leu Leu Thr Met Met Ser Thr Ser Asn Ser Ala Lys Asp Pro Thr
            260                 265                 270
Val Ala Lys Glu Glu Gln Ile Ser Phe Arg Asp Cys Ala Glu Val Phe
        275                 280                 285
Lys Ser Gly His Thr Thr Asn Gly Ile Tyr Thr Leu Thr Phe Pro Asn
290                 295                 300
Ser Thr Glu Glu Ile Lys Ala Tyr Cys Asp Met Glu Ala Gly Gly Gly
305                 310                 315                 320
Gly Trp Thr Ile Ile Gln Arg Arg Glu Asp Gly Ser Val Asp Phe Gln
                325                 330                 335
Arg Thr Trp Lys Glu Tyr Lys Val Gly Phe Gly Asn Pro Ser Gly Glu
            340                 345                 350
Tyr Trp Leu Gly Asn Glu Phe Val Ser Gln Leu Thr Asn Gln Gln Arg
        355                 360                 365
Tyr Val Leu Lys Ile His Leu Lys Asp Trp Glu Gly Asn Glu Ala Tyr
370                 375                 380
Ser Leu Tyr Glu His Phe Tyr Leu Ser Ser Glu Glu Leu Asn Tyr Arg
385                 390                 395                 400
Ile His Leu Lys Gly Leu Thr Gly Thr Ala Gly Lys Ile Ser Ser Ile
                405                 410                 415
Ser Gln Pro Gly Asn Asp Phe Ser Thr Lys Asp Gly Asp Asn Asp Lys
            420                 425                 430
Cys Ile Cys Lys Cys Ser Gln Met Leu Thr Gly Gly Trp Trp Phe Asp
        435                 440                 445
Ala Cys Gly Pro Ser Asn Leu Asn Gly Met Tyr Tyr Pro Gln Arg Gln
        450                 455                 460
Asn Thr Asn Lys Phe Asn Gly Ile Lys Trp Tyr Trp Lys Gly Ser
465                 470                 475                 480
Gly Tyr Ser Leu Lys Ala Thr Thr Met Met Ile Arg Pro Ala Asp Phe
                485                 490                 495

<210> SEQ ID NO 8
<211> LENGTH: 495
<212> TYPE: PRT
```

<213> ORGANISM: Homo sapiens

<400> SEQUENCE: 8

Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Pro Tyr Val Ser Asn Ala
    50                  55                  60

Val Gln Arg Asp Ala Pro Leu Glu Tyr Asp Asp Ser Val Gln Arg Leu
65                  70                  75                  80

Gln Val Leu Glu Asn Ile Met Glu Asn Asn Thr Gln Trp Leu Met Lys
                85                  90                  95

Leu Glu Asn Tyr Ile Gln Asp Asn Met Lys Lys Glu Met Val Glu Ile
            100                 105                 110

Gln Gln Asn Ala Val Gln Asn Gln Thr Ala Val Met Ile Glu Ile Gly
        115                 120                 125

Thr Asn Leu Leu Asn Gln Thr Ala Glu Gln Thr Arg Lys Leu Thr Asp
130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
        195                 200                 205

Ile Lys Glu Glu Lys Asp Gln Leu Gln Val Leu Val Ser Lys Gln Asn
210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Glu Thr Val Asn
                245                 250                 255

Asn Leu Leu Thr Met Met Ser Thr Ser Asn Ser Lys Asp Pro Thr Val
            260                 265                 270

Ala Lys Glu Glu Gln Ile Ser Phe Arg Asp Cys Ala Glu Val Phe Lys
        275                 280                 285

Ser Gly His Thr Thr Asn Gly Ile Tyr Thr Leu Thr Phe Pro Asn Ser
290                 295                 300

Thr Glu Glu Ile Lys Ala Tyr Cys Asp Met Glu Ala Gly Gly Gly Gly
305                 310                 315                 320

Trp Thr Ile Ile Gln Arg Arg Glu Asp Gly Ser Val Asp Phe Gln Arg
                325                 330                 335

Thr Trp Lys Glu Tyr Lys Val Gly Phe Gly Asn Pro Ser Gly Glu Tyr
            340                 345                 350

Trp Leu Gly Asn Glu Phe Val Ser Gln Leu Thr Asn Gln Gln Arg Tyr
        355                 360                 365

Val Leu Lys Ile His Leu Lys Asp Trp Glu Gly Asn Glu Ala Tyr Ser
370                 375                 380

Leu Tyr Glu His Phe Tyr Leu Ser Ser Glu Glu Leu Asn Tyr Arg Ile
385                 390                 395                 400

```
His Leu Lys Gly Leu Thr Gly Thr Ala Gly Lys Ile Ser Ser Ile Ser
                405                 410                 415

Gln Pro Gly Asn Asp Phe Ser Thr Lys Asp Gly Asp Asn Asp Lys Cys
                420                 425                 430

Ile Cys Lys Cys Ser Gln Met Leu Thr Gly Gly Trp Trp Phe Asp Ala
                435                 440                 445

Cys Gly Pro Ser Asn Leu Asn Gly Met Tyr Tyr Pro Gln Arg Gln Asn
            450                 455                 460

Thr Asn Lys Phe Asn Gly Ile Lys Trp Tyr Tyr Trp Lys Gly Ser Gly
465                 470                 475                 480

Tyr Ser Leu Lys Ala Thr Thr Met Met Ile Arg Pro Ala Asp Phe
                485                 490                 495

<210> SEQ ID NO 9
<211> LENGTH: 191
<212> TYPE: PRT
<213> ORGANISM: Homo sapiens

<400> SEQUENCE: 9

Met Asn Phe Leu Leu Ser Trp Val His Trp Ser Leu Ala Leu Leu Leu
1                   5                   10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
65                  70                  75                  80

Met Arg Cys Gly Gly Cys Ser Asn Asp Glu Gly Leu Glu Cys Val Pro
                85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Asn Pro Cys Gly
        130                 135                 140

Pro Cys Ser Glu Arg Arg Lys His Leu Phe Val Gln Asp Pro Gln Thr
145                 150                 155                 160

Cys Lys Cys Ser Cys Lys Asn Thr His Ser Arg Cys Lys Ala Arg Gln
                165                 170                 175

Leu Glu Leu Asn Glu Arg Thr Cys Arg Cys Asp Lys Pro Arg Arg
                180                 185                 190

<210> SEQ ID NO 10
<211> LENGTH: 207
<212> TYPE: PRT
<213> ORGANISM: Homo sapiens

<400> SEQUENCE: 10

Met Ser Pro Leu Leu Arg Arg Leu Leu Leu Val Ala Leu Leu Gln Leu
1                   5                   10                  15

Ala Arg Thr Gln Ala Pro Val Ser Gln Phe Asp Gly Pro Ser His Gln
                20                  25                  30

Lys Lys Val Val Pro Trp Ile Asp Val Tyr Ala Arg Ala Thr Cys Gln
                35                  40                  45
```

```
Pro Arg Glu Val Val Pro Leu Ser Met Glu Leu Met Gly Asn Val
     50              55                  60

Val Lys Gln Leu Val Pro Ser Cys Val Thr Val Gln Arg Cys Gly Gly
 65              70                  75                  80

Cys Cys Pro Asp Asp Gly Leu Glu Cys Val Pro Thr Gly Gln His Gln
             85                  90                  95

Val Arg Met Gln Ile Leu Met Ile Gln Tyr Pro Ser Ser Gln Leu Gly
         100                 105                 110

Glu Met Ser Leu Glu Glu His Ser Gln Cys Glu Cys Arg Pro Lys Lys
         115                 120                 125

Lys Glu Ser Ala Val Lys Pro Asp Arg Val Ala Ile Pro His His Arg
     130                 135                 140

Pro Gln Pro Arg Ser Val Pro Gly Trp Asp Ser Thr Pro Gly Ala Ser
145                 150                 155                 160

Ser Pro Ala Asp Ile Ile His Pro Thr Pro Ala Pro Gly Ser Ser Ala
                165                 170                 175

Arg Leu Ala Pro Ser Ala Val Asn Ala Leu Thr Pro Gly Pro Ala Ala
                180                 185                 190

Ala Ala Ala Asp Ala Ala Ala Ser Ser Ile Ala Lys Gly Gly Ala
            195                 200                 205
```

```
<210> SEQ ID NO 11
<211> LENGTH: 419
<212> TYPE: PRT
<213> ORGANISM: Homo sapiens

<400> SEQUENCE: 11

Met His Leu Leu Gly Phe Phe Ser Val Ala Cys Ser Leu Leu Ala Ala
 1               5                  10                  15

Ala Leu Leu Pro Gly Pro Arg Glu Ala Pro Ala Ala Ala Ala Ala Phe
             20                  25                  30

Glu Ser Gly Leu Asp Leu Ser Asp Ala Glu Pro Asp Ala Gly Glu Ala
         35                  40                  45

Thr Ala Tyr Ala Ser Lys Asp Leu Glu Glu Gln Leu Arg Ser Val Ser
     50                  55                  60

Ser Val Asp Glu Leu Met Thr Val Leu Tyr Pro Glu Tyr Trp Lys Met
 65              70                  75                  80

Tyr Lys Cys Gln Leu Arg Lys Gly Gly Trp Gln His Asn Arg Glu Gln
             85                  90                  95

Ala Asn Leu Asn Ser Arg Thr Glu Glu Thr Ile Lys Phe Ala Ala Ala
            100                 105                 110

His Tyr Asn Thr Glu Ile Leu Lys Ser Ile Asp Asn Glu Trp Arg Lys
        115                 120                 125

Thr Gln Cys Met Pro Arg Glu Val Cys Ile Asp Val Gly Lys Glu Phe
    130                 135                 140

Gly Val Ala Thr Asn Thr Phe Phe Lys Pro Pro Cys Val Ser Val Tyr
145                 150                 155                 160

Arg Cys Gly Gly Cys Cys Asn Ser Glu Gly Leu Gln Cys Met Asn Thr
                165                 170                 175

Ser Thr Ser Tyr Leu Ser Lys Thr Leu Phe Glu Ile Thr Val Pro Leu
            180                 185                 190

Ser Gln Gly Pro Lys Pro Val Thr Ile Ser Phe Ala Asn His Thr Ser
        195                 200                 205

Cys Arg Cys Met Ser Lys Leu Asp Val Tyr Arg Gln Val His Ser Ile
    210                 215                 220
```

-continued

```
Ile Arg Arg Ser Leu Pro Ala Thr Leu Pro Gln Cys Gln Ala Ala Asn
225                 230                 235                 240

Lys Thr Cys Pro Thr Asn Tyr Met Trp Asn Asn His Ile Cys Arg Cys
                245                 250                 255

Leu Ala Gln Glu Asp Phe Met Phe Ser Ser Asp Ala Gly Asp Asp Ser
            260                 265                 270

Thr Asp Gly Phe His Asp Ile Cys Gly Pro Asn Lys Glu Leu Asp Glu
        275                 280                 285

Glu Thr Cys Gln Cys Val Cys Arg Ala Gly Leu Arg Pro Ala Ser Cys
    290                 295                 300

Gly Pro His Lys Glu Leu Asp Arg Asn Ser Cys Gln Cys Val Cys Lys
305                 310                 315                 320

Asn Lys Leu Phe Pro Ser Gln Cys Gly Ala Asn Arg Glu Phe Asp Glu
                325                 330                 335

Asn Thr Cys Gln Cys Val Cys Lys Arg Thr Cys Pro Arg Asn Gln Pro
            340                 345                 350

Leu Asn Pro Gly Lys Cys Ala Cys Glu Cys Thr Glu Ser Pro Gln Lys
        355                 360                 365

Cys Leu Leu Lys Gly Lys Lys Phe His His Gln Thr Cys Ser Cys Tyr
370                 375                 380

Arg Arg Pro Cys Thr Asn Arg Gln Lys Ala Cys Glu Pro Gly Phe Ser
385                 390                 395                 400

Tyr Ser Glu Glu Val Cys Arg Cys Val Pro Ser Tyr Trp Lys Arg Pro
                405                 410                 415

Gln Met Ser

<210> SEQ ID NO 12
<211> LENGTH: 354
<212> TYPE: PRT
<213> ORGANISM: Homo sapiens

<400> SEQUENCE: 12

Met Tyr Arg Glu Trp Val Val Asn Val Phe Met Met Leu Tyr Val
1               5                   10                  15

Gln Leu Val Gln Gly Ser Ser Asn Glu His Gly Pro Val Lys Arg Ser
                20                  25                  30

Ser Gln Ser Thr Leu Glu Arg Ser Glu Gln Gln Ile Arg Ala Ala Ser
            35                  40                  45

Ser Leu Glu Glu Leu Leu Arg Ile Thr His Ser Glu Asp Trp Lys Leu
        50                  55                  60

Trp Arg Cys Arg Leu Arg Leu Lys Ser Phe Thr Ser Met Asp Ser Arg
65                  70                  75                  80

Ser Ala Ser His Arg Ser Thr Arg Phe Ala Ala Thr Phe Tyr Asp Ile
                85                  90                  95

Glu Thr Leu Lys Val Ile Asp Glu Glu Trp Gln Arg Thr Gln Cys Ser
                100                 105                 110

Pro Arg Glu Thr Cys Val Glu Val Ala Ser Glu Leu Gly Lys Ser Thr
            115                 120                 125

Asn Thr Phe Phe Lys Pro Pro Cys Val Asn Val Phe Arg Cys Gly Gly
        130                 135                 140

Cys Cys Asn Glu Glu Ser Leu Ile Cys Met Asn Thr Ser Thr Ser Tyr
145                 150                 155                 160

Ile Ser Lys Gln Leu Phe Glu Ile Ser Val Pro Leu Thr Ser Val Pro
                165                 170                 175
```

```
Glu Leu Val Pro Val Lys Val Ala Asn His Thr Gly Cys Lys Cys Leu
            180                 185                 190

Pro Thr Ala Pro Arg His Pro Tyr Ser Ile Ile Arg Arg Ser Ile Gln
            195                 200                 205

Ile Pro Glu Glu Asp Arg Cys Ser His Ser Lys Lys Leu Cys Pro Ile
            210                 215                 220

Asp Met Leu Trp Asp Ser Asn Lys Cys Lys Cys Val Leu Gln Glu Glu
225                 230                 235                 240

Asn Pro Leu Ala Gly Thr Glu Asp His Ser His Leu Gln Glu Pro Ala
                245                 250                 255

Leu Cys Gly Pro His Met Met Phe Asp Glu Asp Arg Cys Glu Cys Val
            260                 265                 270

Cys Lys Thr Pro Cys Pro Lys Asp Leu Ile Gln His Pro Lys Asn Cys
            275                 280                 285

Ser Cys Phe Glu Cys Lys Glu Ser Leu Glu Thr Cys Cys Gln Lys His
            290                 295                 300

Lys Leu Phe His Pro Asp Thr Cys Ser Cys Glu Asp Arg Cys Pro Phe
305                 310                 315                 320

His Thr Arg Pro Cys Ala Ser Gly Lys Thr Ala Cys Ala Lys His Cys
                325                 330                 335

Arg Phe Pro Lys Glu Lys Arg Ala Ala Gln Gly Pro His Ser Arg Lys
            340                 345                 350

Asn Pro

<210> SEQ ID NO 13
<211> LENGTH: 20
<212> TYPE: DNA
<213> ORGANISM: Artificial Sequence
<220> FEATURE:
<223> OTHER INFORMATION: A synthetic primer

<400> SEQUENCE: 13
gtcgtaccac tggcattgtc                                              20

<210> SEQ ID NO 14
<211> LENGTH: 20
<212> TYPE: DNA
<213> ORGANISM: Artificial Sequence
<220> FEATURE:
<223> OTHER INFORMATION: A synthetic primer

<400> SEQUENCE: 14
accctcatag atgggcacag                                              20

<210> SEQ ID NO 15
<211> LENGTH: 20
<212> TYPE: DNA
<213> ORGANISM: Artificial Sequence
<220> FEATURE:
<223> OTHER INFORMATION: A synthetic primer

<400> SEQUENCE: 15
tccggcgagg agtctaacta                                              20

<210> SEQ ID NO 16
<211> LENGTH: 20
<212> TYPE: DNA
<213> ORGANISM: Artificial Sequence
<220> FEATURE:
<223> OTHER INFORMATION: A synthetic primer
```

```
<400> SEQUENCE: 16
agctggaaaa gcagaagctg                                                  20

<210> SEQ ID NO 17
<211> LENGTH: 20
<212> TYPE: DNA
<213> ORGANISM: Artificial Sequence
<220> FEATURE:
<223> OTHER INFORMATION: A synthetic primer

<400> SEQUENCE: 17
tgcctacctc acctgtttcc                                                  20

<210> SEQ ID NO 18
<211> LENGTH: 20
<212> TYPE: DNA
<213> ORGANISM: Artificial Sequence
<220> FEATURE:
<223> OTHER INFORMATION: A synthetic primer

<400> SEQUENCE: 18
tctgtctggc tgtcatctgg                                                  20
```

PROTECTION OF CARDIAC MYOCARDIUM

RELATED APPLICATIONS

This application is a continuation-in-part under 35 U.S.C. § 111(a) of International Application No. PCT/US03/36644 filed Nov. 14, 2003 and published in English as WO 2004/045531 on Jun. 3, 2004, which claimed priority from Provisional Application No. 60/426,124, filed Nov. 14, 2002, which applications and publication are incorporated herein by reference.

Work relating to this application was supported by grant numbers AG 19738, AG20918 and HL67839 from the National Institutes of Health. Accordingly the United States government has certain rights in the invention.

BACKGROUND OF THE INVENTION

Ischemic heart disease is the most common cause of morbidity and mortality in the population over the age of sixty-five. Sullivan, L. W. 1990. Healthy people 2000. *N Engl J. Med.* 323:1065-1067; Wei, J. Y. 1992. Age and the cardiovascular system. *N Engl J. Med.* 327:1735-1739; Association, A. H. 1993-1995. Heart and stroke facts statistical supplement/1994-1996. Dallas, Tex. The Association. Acute disruption of coronary blood flow causes apoptotic and necrotic death of myocardial endothelial cells and myocyte resulting in thinning of the ventricular wall, and leading to impairment of cardiac function. Cheng, W. et al. Programmed myocyte cell death affects the viable myocardium after infarction in rats. *Exp Cell Res* 226, 316-27 (1996). New strategies are therefore needed to prevent and reduce the pathology of cardiovascular disease associated with advancing age.

The inventors have recently demonstrated that platelet-derived growth factor (PDGF) can reduce or limit the extent of myocardial necrosis induced by ligation of the left anterior descending artery (LAD) in the rat heart. Edelberg, J. M. et al. *Circulation* 105, 608-13 (2002). However, PDGF treatment was most effective when administered prior to, and not at the time of, coronary occlusion. Hence, new compositions and treatment methods are needed to expand the therapeutic window of platelet-derived growth factor and to optimally protect cardiac tissues during occlusion of coronary vessels.

SUMMARY OF THE INVENTION

The invention provides compositions and methods for protecting vascular tissue in a patient from damage, for example, during occlusion of an artery. In some embodiments, the compositions and methods are used to prevent or treat tissue injuries resulting from myocardial infarction.

The methods of the invention involve administering to the patient a composition comprising a therapeutically effective amount of platelet-derived growth factor, angiopoietin-2, and vascular endothelial growth factor. The composition can also include a pharmaceutically acceptable carrier.

In one embodiment, the invention provides a method of promoting vascular health in a patient by administering to the patient a therapeutically effective amount of platelet derived growth factor, angiopoietin-2, and vascular endothelial growth factor.

In another embodiment, the invention provides a method of protecting cardiac tissue in a patient from damage during myocardial infarction by administering to the patient a therapeutically effective amount of platelet derived growth factor, angiopoietin-2, and vascular endothelial growth factor.

In yet another embodiment, the invention provides a method of improving survival of transplanted tissue in a patient by administering to the patient a therapeutically effective amount of platelet derived growth factor, angiopoietin-2, and vascular endothelial growth factor.

Administration can be parenteral, as by intravascular, intravenous, intraarterial, intraperitoneal, intraventricular infusion, stent, infusion catheter, balloon catheter, bolus injection, topical administration as by direct application to tissue surfaces during surgery, or oral. Alternatively, administration can be directly into the heart or into the vasculature of the patient.

The platelet-derived growth factor employed can, for example, be platelet derived growth factor AB, platelet derived growth factor A, platelet derived growth factor B, or mixtures thereof. In some embodiments, the platelet-derived growth factor can have a sequence comprising SEQ ID NO:1, SEQ ID NO:2, SEQ ID NO:3, SEQ ID NO:4, SEQ ID NO:5, SEQ ID NO:6 or a mixture thereof. The angiopoietin-2 can, for example, have a sequence comprising SEQ ID NO:7, SEQ ID NO:8, or a mixture thereof. The vascular endothelial growth factor can, for example, have a sequence comprising SEQ ID NO:9, SEQ ID NO:10, SEQ ID NO:11, SEQ ID NO:12 or a mixture thereof.

The size of necrosis, vascular injury or myocardial infarction in the patient can be reduced by such compositions and methods of the invention.

DESCRIPTION OF THE FIGURES

FIG. 2A provides representative sections of PDGF or PBS treated hearts that were stained for either VEGF or Ang-2. The arrows indicate which cells stain positively for VEGF or Ang-2. FIG. 2B provides a graph comparing the vessel profile numbers of VEGF or Ang-2 positively stained cells in PDGF or PBS treated hearts sections. Positive vessels were counted in six different fields on each slide (magnification 40×) (N=3), mean profile numbers were compared using the Student's T-test. There was significant induction of both VEGF and Ang-2 in PDGF treated hearts compared to PBS treated hearts. A value of p<0.05 (*) was observed for PDGF treatment vs. PBS treatment.

FIG. 4A-E illustrates that hearts treated with a combination of PDGF plus VEGF and Ang-2 (PVA) have fewer apoptotic cells than hearts treated with PDGF alone, a combination of PDGF plus Ang-2 or a combination of PDGF plus VEGF. FIGS. 4A and C provide representative sections of the rat anterior left ventricular wall that were TUNEL stained to detect apoptotic cells, and the star (*) symbols indicate which part of each section was examined under higher magnification for apoptotic cells in FIGS. 4B and 4D, respectively. FIG. 4E is a bar graph summarizing the mean apoptotic cell density observed under high magnification in sections of the rat anterior left ventricular wall injected with PBS, PDGF (P), PDGF plus VEGF and Ang-2 (PVA), PDGF plus VEGF (PV), PDGF plus Ang-2 (PA) or VEGF plus Ang-2 (VA) (n=3, each group) at the time of coronary occlusion. *P<0.05 PVA vs. all other groups

FIGS. 6A-B provide the graphs illustrating a real time RT-PCR analysis of VEGF and Ang-2 transcripts in PDGF-AB treated 4 and 24-month-old rat cardiac microvascular endothelial cells (CMECs) in vitro. FIG. 6C provides images of representative cardiac capillary sections from rat hearts injected with vehicle (PBS) or PDGF-AB 24 hr before euthanization. The sections were immunohistochemically stained for VEGF or Ang-2 (n=3, each); Bar=10 μm. FIG. 6D provides a graph showing the densities of VEGF and Ang-2 positive capillaries in PDGF-AB (shaded bars) or PBS treated hearts (open bars). *p<0.05, **p<0.005 treatment vs. control.

FIG. 7A provides images of representative cardiac capillary sections from 4- and 24-month-old rat hearts injected with vehicle (PBS) or PDGF-AB 24 hr before euthanization. The sections were immunohistochemically stained for PDGFR-α, Flk-1, or Tie-2 (n=3, each); Bar=10 μm. FIG. 7B provides a bar graph showing the densities of PDGFR-α, Flk-1, and Tie-2 positive capillaries (mm$^2$) in PDGF-AB or PBS treated hearts. *P<0.05 PDGF-AB vs. PBS.

FIG. 8A provides representative examples of neonatal cardiac tissues transplanted into senescent hosts (18-month-old) with pretreatment of VEGF (100 ng) or VEGF (100 ng) and PDGF-AB (3 ng). The arrowhead indicates the site of necrotic loss of both allograft and host pinnal tissue beyond the transplant site in the majority of the VEGF pretreated transplants. The arrow indicates viable/intact cardiac transplants in the host pinnal tissue. FIG. 8B illustrates a dose response curve of PDGF-AB pretreatment in the restoration of cardiac allograft viability in 18-month-old mice (n≧20, per group). 10 ng and 100 ng of PDGF-AB restored a significant number of allografts compared with 0 and 1 ng doses, P<0.005. FIG. 8C provides an assessment of VEGF and Ang-2 pretreatment versus combined VEGF and PDGF-AB pretreatment for 24 hr (n≧20, per group). *P<0.05 PDGF-AB (3 ng) vs. PBS. P<0.01 Treatment vs. PDGF-AB (3 ng) or PBS. FIG. 8D** provides an assessment of the effects of different cytokine combinations upon the peri-transplantation of pinnal tissue when the cytokines are given at the time of cardiac allograft transplantation (n≧10, per group). *P<0.05 PDGF-AB plus VEGF plus Ang-2 vs. PBS and all other treatment groups.

FIG. 9 illustrates that synergistic suppression of cardiac apoptosis post coronary occlusion. Apoptosis was observed by TUNEL labeling of rat cardiac sections taken 24 hr after injection, at the time of LAD ligation, with combinations of PDGF-AB, VEGF and Ang-2. FIG. 9A shows a reconstructed cross-section micrograph from lower magnification (4×) images for measurement of apoptotic area (% of left ventricular area). FIG. 9B provides a higher magnification (40×) TUNEL staining images employed in the quantification of apoptotic cell density (Bar=10 μm). FIG. 9C provides a bar graph showing the mean apoptotic risk area size (white bars) and cell density [TUNEL(+)] (black bars) in the sections of rat anterior left ventricular wall injected with PBS, PDGF-AB, PDGFAB plus VEGF (PV), PDGF-AB plus Ang-2 (PA) or VEGF plus Ang-2 (VA) or PDGF-AB plus VEGF and Ang-2 (PVA), (n=3, each group) at the time of LAD ligation. *P<0.01 and **P<0.005 PVA vs. PBS and all other cytokine groups.

FIG. 10 shows that while cardioprotection by combined cytokine injection at the time of coronary occlusion is age-associated, the combination of PDGF-AB plus VEGF and Ang-2 can still reduce the size of myocardial infarctions in older (24 mo.) animals.

DETAILED DESCRIPTION OF THE INVENTION

Figure 1:
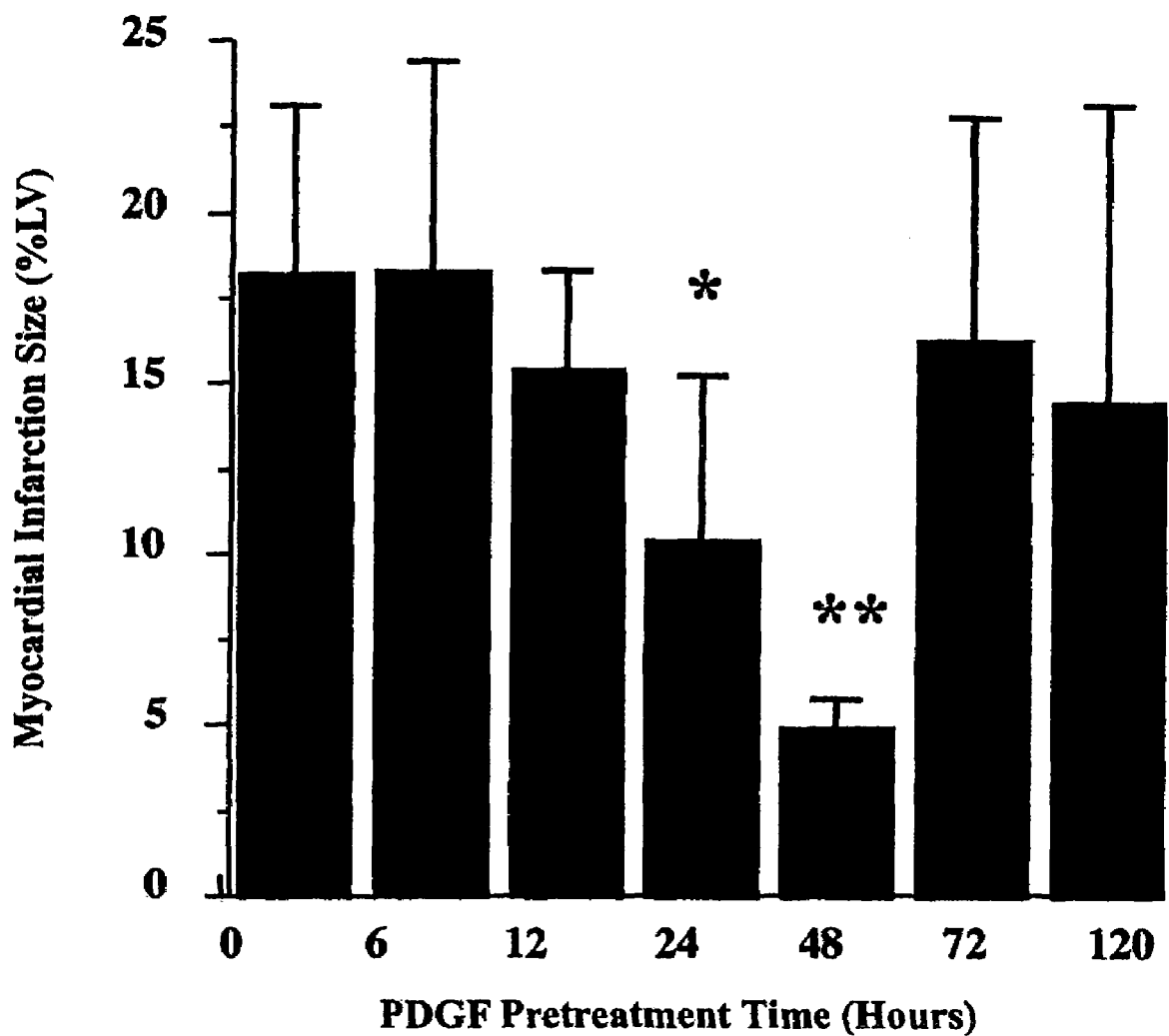
FIG. 1 provides a bar graph showing when PDGF pretreatment is most effective in protecting heart tissue from myocardial infraction (MI). Rat hearts were treated with intramyocardial injection of PDGF, and LAD ligations were performed either at the time of injection (0 hr), or 6, 12, 24, 48, 72 or 120 hr after injection. Myocardial infarction size was scored on Masson's trichrome stained slides. The mean values of relative area size of myocardial necrosis to area size of left ventricular myocardium were compared. PDGF was most effective when administered at 24 to 48 hr before myocardial infarction-a statistically significant reduction in the size of the myocardial infarction was observed when PDGF pretreatment was performed at 24 hr or 48 hr before ligation. PDGF injection at the time of ligation or at 6 and 12 hr before ligation failed to provide significant protection. The cardioprotective effect of PDGF pretreatment also seemed to expire 72 hours after injection. A value of p<0.05 (*) was observed for 24 hr pretreatment vs. all other groups. A value of p<0.05 (**) was observed for 48 hr pretreatment vs. all other groups.

The present invention provides pharmaceutical compositions comprising an effective amount of platelet-derived growth factor (PDGF), angiopoietin-2 (Ang-2) and vascular endothelial growth factor (VEGF) that are effective for preventing damage to cardiac tissues as a result of vascular conditions or diseases, for example, those conditions and diseases that can lead to occlusion of an artery. Such administration is given before, during or as soon as possible after arterial occlusion.

Vascular Diseases

The vascular diseases treated by the present invention are vascular diseases of mammals. The word mammal means any mammal. Some examples of mammals include, for example, pet animals, such as dogs and cats; farm animals, such as pigs, cattle, sheep, and goats; laboratory animals, such as mice and rats; primates, such as monkeys, apes, and chimpanzees; and humans.

According to the invention, endothelial cells within normal vascular tissues change as they grow older, exhibiting reduced angiogenesis and losing their ability to communicate with other cells by secreting signaling agents. These changes can lead to a diminished capacity for blood vessel formation, a reduction in blood flow to the associated organ or system, and an inability to recover from injuries or diseases that can block or adversely affect blood vessels.

Many pathological conditions can lead to vascular diseases that can block blood vessels such as atherosclerosis, preeclampsia, peripheral vascular disease, erectile dysfunction, cancers, renal failure, heart disease, and stroke. Such conditions are associated with alterations in the normal vascular condition of the affected tissues and/or systems.

Accordingly, this invention relates to methods for treating endothelial dysfunction, such as a vascular condition or a circulatory condition associated with loss, injury or disruption of the vasculature within an anatomical site or system. The term "vascular condition" or "vascular disease" refers to a state of vascular tissue where blood flow is, or can become, impaired or even blocked.

Examples of vascular conditions or vascular disease to which the methods of the invention apply are those in which the vasculature of the affected tissue or system is injured, senescent, or otherwise altered in some way, so that blood flow to the tissue or system is reduced or is in danger of being reduced. Vascular, circulatory or hypoxic conditions to which the methods of the invention apply are those associated with, but not limited to, myocardial infarction, maternal hypoxia (e.g., placental hypoxia, preeclampsia), abnormal pregnancy, peripheral vascular disease (e.g., arteriosclerosis), transplant accelerated arteriosclerosis, deep vein thrombosis, erectile dysfunction, cancers, renal failure, stroke, heart disease, sleep apnea, hypoxia during sleep, female sexual dysfunction, fetal hypoxia, respiratory disorders due to smoking, anemia, hypovolemia, vascular or circulatory conditions which increase risk of metastasis or tumor progression, hemorrhage, hypertension, diabetes, vasculopathologies, disorders due to surgery (e.g., per-surgical hypoxia, post-operative hypoxia), Raynaud's disease, endothelial dysfunction, regional perfusion deficits (e.g., limb, gut, renal ischemia), stroke, thrombosis, frost bite, decubitus ulcers, asphyxiation, poisoning (e.g., carbon monoxide, heavy metal), altitude sickness, pulmonary hypertension, sudden infant death syndrome (SIDS), asthma, chronic obstructive pulmonary disease (COPD), congenital circulatory abnormalities (e.g., Tetralogy of Fallot) and erythroblastosis (blue baby syndrome). In particular embodiments, the invention provides methods of treating loss of circulation or endothelial dysfunction in a mammal such as a human patient.

Thus, the invention is directed to methods of promoting vascular health by preventing or treating diseases or conditions like those listed above. In some embodiments, the disease or condition is stroke, atherosclerosis, acute coronary syndromes including unstable angina, thrombosis and myocardial infarction, plaque rupture, both primary and secondary (in-stent) restenosis in coronary or peripheral arteries, transplantation-induced sclerosis, peripheral limb disease, intermittent claudication and diabetic complications (including ischemic heart disease, peripheral artery disease, congestive heart failure, retinopathy, neuropathy and nephropathy), or thrombosis.

In some embodiments, the vascular condition or vascular disease arises from injured or damaged myocardium. As used herein injured or damaged myocardium refers to myocardial cells that have been exposed to ischemic conditions. These ischemic conditions may be caused by a myocardial infarction, transplant injury, heart surgery or cardiovascular disease. The lack of oxygen causes the death of the cells in the surrounding area, leaving an infarct that can eventually scar.

Preferably, injured or damaged myocardium is treated with the methods and compositions of the invention before damage occurs (e.g. when damage is suspected of occurring or a possibility exists of potential vascular injury), during injury or as quickly as possible after injury or damage occurs. Hence, the methods and compositions of the invention are advantageously employed on tissues that may be experiencing, are experiencing, have just experienced or are in danger of ischemia, myocardial infarction, heart attack or loss of blood flow. The methods and compositions of the invention are also advantageously employed on recently damaged vascular tissues (e.g. myocardium) and on not so recently damaged vascular tissues (e.g. myocardium).

As used herein "recently damaged vascular tissues" refers to vascular tissues (or myocardium) that has been damaged within zero to one day of treatment being started. In a preferred embodiment, the tissue (or myocardium) has been damaged within zero to twelve hours of the start of treatment. In a further preferred embodiment, the tissue or myocardium has been damaged within 6 hours of the start of treatment.

The methods and compositions of the invention can be used to prevent or to treat vascular conditions such as those listed above. These methods involve administering an effective amount of a combination of platelet-derived growth factor (PDGF), angiopoietin-2 (Ang-2) and vascular endothelial growth factor (VEGF). Such an effective amount is effective when it reduces the extent of damage due to vascular injury, vascular occlusion or myocardial infarction.

Platelet-Derived Growth Factor

Naturally occurring, platelet-derived growth factor ("PDGF") is a disulfide-bonded dimer having two polypeptide chains, namely the "A" and "B" chains, with the A chain being approximately 60% homologous to the B chain. Naturally occurring PDGF is found in three dimeric forms, namely PDGF-AB heterodimer, PDGF-BB homodimer, or PDGF-AA homodimer. Hannink et al., Mol. Cell. Biol., 6, 1304-1314 (1986). PDGF-AB has been identified as the predominant naturally occurring form. However, some data indicates that the PDGF-BB homodimer may be effective for wound healing. Each monomeric subunit of the biologically active dimer, irrespective of whether it is an A chain monomer or a B chain monomer, contains eight cysteine residues. Some of these cysteine residues form interchain disulfide bonds that hold the dimer together. As used herein, the term PDGF means any PDGF polypeptide or protein, including PDGF A, PDGF B, PDGF AB, PDGF BB, and PDGF AA.

The A polypeptide of human PDGF can be any mammalian PDGF A polypeptide including, for example, human, mouse, rat, rabbit, goat, bovine, horse, sheep and any other mammalian PDGF A polypeptide. The following sequence is one example of an amino acid sequence of a human PDGF A polypeptide (SEQ ID NO:1):

```
  1 MRTWACLLLL GCGYLAHALA EEAEIPRELI ERLARSQIHS

41 IRDLQRLLEI DSVGAEDALE TNLRAHGSHT VKHVPEKRPV

81 PIRRKRSIEE AIPAVCKTRT VIYEIPRSQV DPTSANFLIW

121 PPCVEVKRCT GCCNTSSVKC QPSRVHHRSV KVAKVEYVRK

161 KPKLKEVQVR LEEHLECACA TSNLNPDHRE EETGRRRESG

201 KKRK
```

The following sequence is an example of a mouse PDGF A sequence (SEQ ID NO:2).

```
  1 MRTWACLLLL GCGYLAHALA EEAEIPRELI ERLARSQIHS
 41 IRDLQRLLEI DSVGAEDALE TSLRARGSHA INHVPEKRPV
 81 PIRRKRSIEE AVPAVCKTRT VIYEIPRSQV DPTSANFLIW
121 PPCVEVKRCT GCCNTSSVKC QPSRVHHRSV KVAKVEYVRK
161 KPKLKEVQVR LEEDLECACA TSNLNPDHRE EETDVR
```

Other sequences for PDGF A can readily be obtained by one of skill in the art, for example, from the GenBank database of sequences. Variability in these and other sequences is permitted so long as the PDGF A polypeptide can dimerize with PDGF B and/or function in cell-to-cell communication.

The PDGF B polypeptide found in human platelets has been identified as a 109 amino acid cleavage product (PDGF-$B_{109}$) of a 241 amino acid precursor polypeptide Johnsson et al., EMBO Journal, 3(5), 921-928 (1984). An example of a human sequence for the PDGF B polypeptide is provided below (SEQ ID NO:3).

```
  1 MNRCWALFLS LCCYLRLVSA EGDPIPEELY EMLSDHSIRS
 41 FDDLQRLLHG DPGEEDGAEL DLNMTRSHSG GELESLARGR
 82 RSLGSLTIAE PAMIAECKTR TEVFEISRRL IDRTNANFLV
121 WPPCVEVQRC SGCCNNRNVQ CRPTQVQLRP VQVRKIEIVR
161 KKPIFKKATV TLEDHLACKC ETVAAARPVT RSPGGSQEQR
201 AKTPQTRVTI RTVRVRRPPK GKHRKFKHTH DKTALKETLG
241 A
```

The following sequence is an example of a mouse PDGF B sequence (SEQ ID NO:4).

```
  1 MNRCWALFLP LCCYLRLVSA EGDPIPEELY EMLSDHSIRS
 41 FDDLQRLLHR DSVDEDGAEL DLNMTRAHSG VELESSSRGR
 81 RSLGSLAAAE PAVIAECKTR TEVFQISRNL IDRTNANFLV
121 WPPCVEVQRC SGCCNNRNVQ CRASQVQMRP VQVRKIEIVR
161 KKPIFKKATV TLEDHLACKC ETIVTPRPVT RSPGTSREQR
201 AKTPQARVTI RTVRIRRPPK GKHRKFKHTH DKAALKETLG
241 A
```

A 109 amino acid PDGF B polypeptide is believed to be the mature form of PDGF in humans and constitutes a cleavage product of the PDGF-B precursor protein. Homology with the precursor protein begins at amino acid 82 of the 241 amino acid precursor protein and continues for 109 amino acids yielding, for example, a polypeptide with the following sequence (SEQ ID NO:5):

```
 82 RSLGSLTIAE PAMIAECKTR TEVFEISRRL IDRTNANFLV
121 WPPCVEVQRC SGCCNNRNVQ CRPTQVQLRP VQVRKIEIVR
161 KKPIFKKATV TLEDHLACKC ETVAAARPVT RSPGGSQEQR
201 AKTPQTRVTI RTVRVRRPPK GKHRKFKHTH DKTALKETLG
241 A
```

Another form of PDGF-B (PDGF-$B_{119}$), corresponds to the first 119 amino acids of the PDGF-B precursor protein (SEQ ID NO:6):

```
  1 MNRCWALFLS LCCYLRLVSA EGDPIPEELY EMLSDHSIRS
 41 FDDLQRLLHG DPGEEDGAEL DLNMTRSHSG GELESLARGR
 82 RSLGSLTIAE PAMIAECKTR TEVFEISRRL IDRTNANFL
```

This PDGF-$B_{119}$ form has also been identified as a major cleavage product of the precursor protein when the entire gene is expressed in a transfected mammalian host. See U.S. Pat. No. 5,149,792.

Human platelet-derived growth factor is believed to be the major mitogenic growth factor in serum for connective tissue cells. PDGF can positively affect mitogenesis in arterial smooth muscle cells, fibroblast cells lines, and glial cells. Deuel et al., J. Biol. Chem., 256(17), 8896-8899 (1981). See also, e.g., Heldin et al., J. Cell Physiol., 105, 235 (1980) (brain glial cells); Raines and Ross, J. Biol. Chem., 257, 5154 (1982) (monkey arterial smooth muscle cells). PDGF is also believed to be a chemoattractant for fibroblasts, smooth muscle cells, monocytes, and granulocytes.

Angiopoietin-2

An angiogenic factor, which was originally called TIE-2 ligand-1 (TL1), but which is also referred to as angiopoietin-1 (Ang1) is required for normal vascular development in the mouse. Angiopoietin-2 (also called TIE-2 ligand-2, TL2) is believed to be a naturally occurring antagonist for Ang1 and the angiopoietin-2 receptor. A description of the cloning and sequencing of TL1 (Ang1) and TL2 (Ang2) as well as for methods of making and uses thereof is provided in PCT International Publication No. WO 96/11269 published Apr. 18, 1996, PCT International Publication No. WO 96/31598 published Oct. 10, 1996 and S. Davis, et al., Cell 87: 1161-1169 (1996) each of which is hereby incorporated by reference.

One example of a sequence of a human angiopoietin-2 precursor polypeptide is as follows (SEQ ID NO:7):

```
  1 MWQIVFFTLS CDLVLAAAYN NFRKSMDSIG KKQYQVQHGS
 41 CSYTFLLPEM DNCRSSSSPY VSNAVQRDAP LEYDDSVQRL
 81 QVLENIMENN TQWLMKLENY IQDNMKKEMV EIQQNAVQNQ
121 TAVMIEIGTN LLNQTAEQTR KLTDVEAQVL NQTTRLELQL
161 LEHSLSTNKL EKQILDQTSE INKLQDKNSF LEKKVLAMED
201 KHIIQLQSIK EEKDQLQVLV SKQNSIIEEL EKKIVTATVN
241 NSVLQKQQHD LMETVNNLLT MMSTSNSAKD PTVAKEEQIS
281 FRDCAEVFKS GHTTNGIYTL TFPNSTEEIK AYCDMEAGGG
321 GWTTIQRRED GSVDFQRTWK EYKVGFGNPS GEYWLGNEFV
361 SQLTNQQRYV LKIHLKDWEG NEAYSLYEHF YLSSEELNYR
401 IHLKGLTGTA GKISSISQPG NDFSTKDGDN DKCICKCSQM
441 LTGGWWFDAC GPSNLNGMYY PQRQNTNKFN GIKWYYWKGS
481 GYSLKATTMM IRPADF
```

Another example of a sequence of a human angiopoietin-2 precursor polypeptide is as follows (SEQ ID NO:8):

```
  1 MWQIVFFTLS CDLVLAAAYN NFRKSMDSIG KKQYQVQHGS
 41 CSYTFLLPEM DNCRSSSSPY VSNAVQRDAP LEYDDSVQRL
 81 QVLENIMENN TQWLMKLENY IQDNMKKEMV EIQQNAVQNQ
121 TAVMIEIGTN LLNQTAEQTR KLTDVEAQVL NQTTRLELQL
161 LEHSLSTNKL EKQILDQTSE INKLQDKNSF LEKKVLAMED
201 KHIIQLQSIK EEKDQLQVLV SKQNSIIEEL EKKIVTATVN
241 NSVLQKQQHD LMETVNNLLT MMSTSNSKDP TVAKEEQISF
281 RDCAEVFKSG HTTNGIYTLT FPNSTEEIKA YCDMEAGGGG
321 WTIIQRREDG SVDFQRTWKE YKVGFGNPSG EYWLGNEFVS
361 QLTNQQRYVL KIHLKDWEGN EAYSLYEHFY LSSEELNYRI
401 HLKGLTGTAG KISSISQPGN DFSTKDGDND KCICKCSQML
441 TGGWWFDACG PSNLNGMYYP QRQNTNKFNG IKWYYWKGSG
481 YSLKATTMMI RPADF
```

Vascular Endothelial Growth Factor

Vascular endothelial growth factor (VEGF) (Ferrara et al., Endo. Rev., 13: 18-32 [1992]) is a potent angiogenic factor that acts via the endothelial cell-specific receptor tyrosine kinases fms-like tyrosine kinase (Flt1) and fetal liver kinase (Flk1) (also designated KDR). Shibuya et al., Oncogene, 5: 519-524 (1990); Devries et al., Science, 255: 989-991 (1992); Quinn et al., Proc. Natl. Acad. Sci. USA, 90: 7533-7537 (1993); Millauer et al., Cell, 72: 835-846 (1993); Matthews et al., Proc. Natl. Acad. Sci. USA, 88: 9026-9030 (1991); Terman et al., Biochem. Biophys. Res. Commun., 187: 1579-1586 (1992); Terman et al., Oncogene, 6: 1677-1683 (1991); Oelrichs et al., Oncogene, 8: 11-18 (1993). These two VEGF receptors and a third orphan receptor, Flt4 (Pajusola et al., Cancer Res., 52: 5738-5743 [1992]; Galland et al., Oncogene, 8: 1233-1240 [1993]; Finnerty et al., Oncogene, 8: 2293-2298 [1993]) constitute a subfamily of class III receptor tyrosine kinases that contain seven extracellular immunoglobulin-like domains and a split intracellular tyrosine kinase domain. Mustonen and Alitalo, J. Cell. Biol., 129: 895-898 (1995). See also WO 94/10202 published May 11, 1994 and PCT/US93/00586 filed Jan. 22, 1993 (Avraham et al.). These three receptors have 31-36% amino acid identity in their extracellular ligand-binding domains.

VEGF is a homodimeric, cysteine-rich protein that can occur in at least four forms due to alternative splicing of its mRNA. Ferrara et al., Endo. Rev., 13: 18-32 [1992]). One example of a VEGF polypeptide that may be used in the invention is a polypeptide of the following sequence (SEQ ID NO:9):

```
  1 MNFLLSWVHW SLALLLYLHH AKWSQAAPMA EGGGQNHHEV
 41 VKFMDVYQRS YCHPIETLVD IFQEYPDEIE YIFKPSCVPL
 81 MRCGGCSNDE GLECVPTEES NITMQIMRIK PHQGQHIGEM
121 SFLQHNKCEC RPKKDRARQE NPCGPCSERR KHLFVQDPQT
161 CKCSCKNTHS RCKARQLELN ERTCRCDKPR R
```

Another example of a VEGF polypeptide that may be used in the invention is vascular endothelial growth factor B precursor, which has the following sequence (SEQ ID NO:10):

```
  1 MSPLLRRLLL VALLQLARTQ APVSQFDGPS HQKKVVPWID
 41 VYARATCQPR EVVVPLSMEL MGNVVKQLVP SCVTVQRCGG
 81 CCPDDGLECV PTGQHQVRMQ ILMIQYPSSQ LGEMSLEEHS
121 QCECRPKKKE SAVKPDRVAI PHHRPQPRSV PGWDSTPGAS
162 SPADIIHPTP APGSSARLAP SAVNALTPGP AAAAADAAAS
201 SIAKGGA
```

Another example of a VEGF polypeptide that may be used in the invention is vascular endothelial growth factor C pre-proprotein, which has the following sequence (SEQ ID NO:11):

```
  1 MHLLGFFSVA CSLLAAALLP GPREAPAAAA AFESGLDLSD
 41 AEPDAGEATA YASKDLEEQL RSVSSVDELM TVLYPEYWKM
 81 YKCQLRKGGW QHNREQANLN SRTEETIKFA AAHYNTEILK
121 SIDNEWRKTQ CMPREVCIDV GKEFGVATNT FFKPPCVSVY
161 RCGGCCNSEG LQCMNTSTSY LSKTLFEITV PLSQGPKPVT
201 ISFANHTSCR CMSKLDVYRQ VHSIIRRSLP ATLPQCQAAN
241 KTCPTNYMWN NHICRCLAQE DFMFSSDAGD DSTDGFHDIC
281 GPNKELDEET CQCVCRAGLR PASCGPHKEL DRNSCQCVCK
321 NKLFPSQCGA NREFDENTCQ CVCKRTCPRN QPLNPGKCAC
361 ECTESPQKCL LKGKKFHHQT CSCYRRPCTN RQKACEPGFS
401 YSEEVCRCVP SYWKRPQMS
```

Another example of a VEGF polypeptide that may be used in the invention is vascular endothelial growth factor D precursor, which has the following sequence (SEQ ID NO:12):

```
  1 MYREWVVVNV FMMLYVQLVQ GSSNEHGPVK RSSQSTLERS
 41 EQQIRAASSL EELLRITHSE DWKLWRCRLR LKSFTSMDSR
 81 SASHRSTRFA ATFYDIETLK VIDEEWQRTQ CSPRETCVEV
121 ASELGKSTNT FFKPPCVNVF RCGGCCNEES LICMNTSTSY
161 ISKQLFEISV PLTSVPELVP VKVANHTGCK CLPTAPRHPY
201 SIIRRSIQIP EEDRCSHSKK LCPIDMLWDS NKCKCVLQEE
241 NPLAGTEDHS HLQEPALCGP HMMFDEDRCE CVCKTPCPKD
281 LIQHPKNCSC FECKESLETC CQKHKLFHPD TCSCEDRCPF
321 HTRPCASGKT ACAKHCRFPK EKRAAQGPHS RKNP
```

As recognized by one of skill in the art, each of the PDGF, angiopoietin-2 and VEGF polypeptides from different mammalian species have similar amino acid sequences. According to the invention any PDGF, angiopoietin-2 and VEGF polypeptide from any mammalian species can be utilized in the practice of the invention so long as the PDGF, angiopoietin-2 and VEGF polypeptide can stimulate endothelial cells to promote angiogenesis.

Compositions

The polypeptides of the invention, including their salts, are preferably administered so as to achieve a reduction in at least one symptom associated with a myocardial infarction, or a decrease in the degree or amount of tissue injury associated with myocardial infarction or heart attack.

To achieve the desired effect(s), the polypeptides or variants thereof, may be administered as single or divided dosages, for example, of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results. The amount administered will vary depending on various factors including, but not limited to, the polypeptides chosen, the disease, the weight, the physical condition, the health, the age of the mammal, whether prevention or treatment is to be achieved, and if the peptide is chemically modified. Such factors can be readily determined by the clinician employing animal models or other test systems that are available in the art.

Administration of the combination of therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of the polypeptides of the invention may be essentially continuous over a pre-selected period of time or may be in a series of spaced doses. Both local and systemic administration is contemplated.

To prepare the composition, polypeptides are synthesized or otherwise obtained, purified as necessary or desired and then lyophilized and stabilized. A given polypeptide can then be adjusted to the appropriate concentration, and optionally combined with other agents. The absolute weight of a given polypeptide included in a unit dose can vary widely. For example, about 0.01 to about 2 g, or about 0.1 to about 500 mg, of the combination of polypeptides of the invention. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Daily doses of the polypeptide combination of the invention can vary as well. Such daily doses can range, for example, from about 0.1 g/day to about 50 g/day, from about 0.1 g/day to about 25 g/day, from about 0.1 g/day to about 12 g/day, from about 0.5 g/day to about 8 g/day, from about 0.5 g/day to about 4 g/day, and from about 0.5 g/day to about 2 g/day.

Thus, one or more suitable unit dosage forms comprising the therapeutic polypeptides of the invention can be administered by a variety of routes including oral, parenteral (including subcutaneous, intravenous, intramuscular and intraperitoneal), rectal, dermal, transdermal, intrathoracic, intrapulmonary and intranasal (respiratory) routes. The therapeutic polypeptides may also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system.

When the therapeutic polypeptides of the invention are prepared for oral administration, they are generally combined with a pharmaceutically acceptable carrier, diluent or excipient to form a pharmaceutical formulation, or unit dosage form. For oral administration, the polypeptides may be present as a powder, a granular formulation, a solution, a suspension, an emulsion or in a natural or synthetic polymer or resin for ingestion of the active ingredients from a chewing gum. The active polypeptides may also be presented as a bolus, electuary or paste. Orally administered therapeutic polypeptides of the invention can also be formulated for sustained release, e.g., the polypeptides can be coated, microencapsulated, or otherwise placed within a sustained delivery device. The total active ingredients in such formulations comprise from 0.1 to 99.9% by weight of the formulation.

By "pharmaceutically acceptable" it is meant a carrier, diluent, excipient, and/or salt that is compatible with the other ingredients of the formulation, and not deleterious to the recipient thereof.

Pharmaceutical formulations containing the therapeutic polypeptides of the invention can be prepared by procedures known in the art using well-known and readily available ingredients. For example, the polypeptide can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface-active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

For example, tablets or caplets containing the polypeptides of the invention can include buffering agents such as calcium carbonate, magnesium oxide and magnesium carbonate. Caplets and tablets can also include inactive ingredients such as cellulose, pre-gelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules containing at least one polypeptide of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets containing one or more polypeptides of the invention are designed to resist disintegration in the stomach and dissolve in the more neutral to alkaline environment of the duodenum.

The therapeutic polypeptides of the invention can also be formulated as elixirs or solutions for convenient oral administration or as solutions appropriate for parenteral administration, for instance by intramuscular, subcutaneous, intraperitoneal or intravenous routes. The pharmaceutical formulations of the therapeutic polypeptides of the invention can also take the form of an aqueous or anhydrous solution or dispersion, or alternatively the form of an emulsion or suspension or salve.

Thus, the therapeutic polypeptides may be formulated for parenteral administration (e.g., by injection, for example, bolus injection or continuous infusion) and may be presented in unit dose form in ampoules, pre-filled syringes, small volume infusion containers or in multi-dose containers. As noted above, preservatives can be added to help maintain the shelve life of the dosage form. The active polypeptides and other ingredients may form suspensions, solutions, or emulsions in oily or aqueous vehicles, and may contain formulatory agents such as suspending, stabilizing and/or dispersing agents. Alternatively, the active polypeptides and other ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable carriers, vehicles and adjuvants that are well known in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol," polyglycols and polyethylene glycols, $C_1$-$C_4$ alkyl esters of short-chain acids, ethyl or isopropyl lactate, fatty acid triglycerides such as the products marketed under the name "Miglyol," isopropyl myristate, animal, mineral and vegetable oils and polysiloxanes.

It is possible to add, if necessary, an adjuvant chosen from antioxidants, surfactants, other preservatives, film forming, keratolytic or comedolytic agents, perfumes, flavorings and colorings. Antioxidants such as t-butylhydroquinone, butylated hydroxyanisole, butylated hydroxytoluene and α-tocopherol and its derivatives can be added.

Also contemplated are combination products that include one or more polypeptides of the present invention and one or more other anti-microbial agents. For example, a variety of antibiotics can be included in the pharmaceutical compositions of the invention, such as aminoglycosides (e.g., streptomycin, gentamicin, sisomicin, tobramycin and amicacin), ansamycins (e.g. rifamycin), antimycotics (e.g. polyenes and benzofuran derivatives), β-lactams (e.g. penicillins and cephalosporins), chloramphenical (including thiamphenol and azidamphenicol), linosamides (lincomycin, clindamycin), macrolides (erythromycin, oleandomycin, spiramycin), polymyxins, bacitracins, tyrothycin, capreomycin, vancomycin, tetracyclines (including oxytetracycline, minocycline, doxycycline), phosphomycin and fusidic acid.

Additionally, the polypeptides are well suited to formulation as sustained release dosage forms and the like. The formulations can be so constituted that they release the active polypeptide, for example, in a particular part of the intestinal or respiratory tract, possibly over a period of time. Coatings, envelopes, and protective matrices may be made, for example, from polymeric substances, such as polylactideglycolates, liposomes, microemulsions, microparticles, nanoparticles, or waxes. These coatings, envelopes, and protective matrices are useful to coat indwelling devices, e.g., stents, catheters, peritoneal dialysis tubing, draining devices and the like.

For topical administration, the therapeutic agents may be formulated as is known in the art for direct application to a target area. Forms chiefly conditioned for topical application take the form, for example, of creams, milks, gels, dispersion or microemulsions, lotions thickened to a greater or lesser extent, impregnated pads, ointments or sticks, aerosol formulations (e.g., sprays or foams), soaps, detergents, lotions or cakes of soap. Other conventional forms for this purpose include wound dressings, coated bandages or other polymer coverings, ointments, creams, lotions, pastes, jellies, sprays, and aerosols. Thus, the therapeutic polypeptides of the invention can be delivered via patches or bandages for dermal administration. Alternatively, the polypeptide can be formulated to be part of an adhesive polymer, such as polyacrylate or acrylate/vinyl acetate copolymer. For long-term applications it might be desirable to use microporous and/or breathable backing laminates, so hydration or maceration of the skin can be minimized. The backing layer can be any appropriate thickness that will provide the desired protective and support functions. A suitable thickness will generally be from about 10 to about 200 microns.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active polypeptides can also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1-85% by weight.

Drops, such as eye drops or nose drops, may be formulated with one or more of the therapeutic polypeptides in an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The therapeutic polypeptide may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid carrier.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions pH 7.0-8.0.

The polypeptides of the invention can also be administered to the respiratory tract. Thus, the present invention also provides aerosol pharmaceutical formulations and dosage forms for use in the methods of the invention. In general, such dosage forms comprise an amount of at least one of the agents of the invention effective to treat or prevent the clinical symptoms of a specific infection, indication or disease. Any statistically significant attenuation of one or more symptoms of an infection, indication or disease that has been treated pursuant to the method of the present invention is considered to be a treatment of such infection, indication or disease within the scope of the invention.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatin or blister packs from which the powder may be administered with the aid of an inhalator, insufflator, or a metered-dose inhaler (see, for example, the pressurized metered dose inhaler (MDI) and the dry powder inhaler disclosed in Newinan, S. P. in *Aerosols and the Lung*, Clarke, S. W. and Davia, D. eds., pp. 197-224, Butterworths, London, England, 1984).

Therapeutic polypeptides of the present invention can also be administered in an aqueous solution when administered in an aerosol or inhaled form. Thus, other aerosol pharmaceutical formulations may comprise, for example, a physiologically acceptable buffered saline solution containing between about 0.1 mg/ml and about 100 mg/ml of one or more of the polypeptides of the present invention specific for the indication or disease to be treated. Dry aerosol in the form of finely divided solid polypeptide that are not dissolved or suspended in a liquid are also useful in the practice of the present invention. Polypeptides of the present invention may be formulated as dusting powders and comprise finely divided particles having an average particle size of between about 1 and 5 µm, alternatively between 2 and 3 µm. Finely divided particles may be prepared by pulverization and screen filtration using techniques well known in the art. The particles may be administered by inhaling a predetermined quantity of the finely divided material, which can be in the form of a powder. It will be appreciated that the unit content of active ingredient or ingredients contained in an individual aerosol dose of each dosage form need not in itself constitute an effective amount for treating the particular infection, indication or disease since the necessary effective amount can be reached by administration of a plurality of dosage units. Moreover, the effective amount may be achieved using less than the dose in the dosage form, either individually, or in a series of administrations.

For administration to the upper (nasal) or lower respiratory tract by inhalation, the therapeutic polypeptides of the invention are conveniently delivered from a nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Nebulizers include, but are not limited to, those described in U.S. Pat. Nos. 4,624,251; 3,703,173; 3,561,444; and 4,635,627. Aerosol delivery systems of the type disclosed herein are available from numerous commercial sources including Fisons Corporation (Bedford, Mass.), Schering Corp. (Kenilworth, N.J.) and American Pharmoseal Co., (Valencia, Calif.). For intra-nasal administration, the therapeutic agent may also be administered via nose drops, a liquid spray, such as via a plastic bottle atomizer or metered-dose inhaler. Typical of atomizers are the Mistometer (Wintrop) and the Medihaler (Riker).

Furthermore, the active ingredients may also be used in combination with other therapeutic agents, for example, pain relievers, anti-inflammatory agents, antihistamines, bronchodilators and the like, whether for the conditions described or some other condition.

The present invention further pertains to a packaged pharmaceutical composition for controlling microbial infections such as a kit or other container. The kit or container holds a therapeutically effective amount of a pharmaceutical composition for controlling cardiac damage and instructions for using the pharmaceutical composition for reducing the effects of myocardial infarction. The pharmaceutical composition includes at least one polypeptide of the present invention, in a therapeutically effective amount such that the effects of myocardial infarction are minimized.

The invention is further illustrated by the following non-limiting Examples.

EXAMPLE 1

The Combination of PDGF, VEGF and Ang-2 Protects Against Tissue Damage After Myocardial Infarction This Example illustrates that the combination of growth factors PDGF, VEGF and Ang-2, when injected about 24-48 hr. prior to myocardial infarction, provides better protection against cardiac tissue damage than does injection of PDGF, VEGF or Ang-2 alone.

Materials and Methods

Animals

Studies employing F344 rats and neonatal and 18-month-old C57BL/6 mice (maintained by Harlan Sprague Dawley, Inc) were performed in compliance with the Institutional Animal Care and Use Committee of Weill Medical College of Cornell University.

Growth Factors

Studies employed intramyocardial injections of PDGF-AB (R & D system, # 222-AB), VEGF and Ang-2.

PDGF Cardioprotection Kinetics

In order to define the therapeutic window of PDGF cardioprotection from myocardial infarction, PDGF (R & D system, # 222-AB) was intramyocardially injected at different time points (0, 6 hr, 12 hr, 24 hr, 48 hr, 72 hr, and 120 hr) prior to coronary ligation. In these experiments, the rats (n=6, time point) were anesthetized and underwent left intercostal thoracotomy. After identifying the left anterior descending artery (LAD), 100 ng of PDGF-AB in 50 µL phosphate buffered saline (PBS) solution was injected through a 30-gauge needle using a 250-µL Hamilton syringe. Two injections (25 µL per injection, 2 mm apart) were made at the mid-left ventricular anterior wall. In the 0 hr set of rats, coronary occlusion was performed at the time of injection. The LAD was ligated just below left atrial appendage with 8-0 nylon sutures. Pallor and regional wall motion abnormality of the left ventricle confirmed occlusion. The chest wall was closed, and after recovery, the rats were returned to the animal facility. For the other time points, the chest walls were closed, the lungs inflated, the rats were extubated, and the tracheotomy closed. At time points between 6 and 120 hr after PDGF injection the sets of the rats were reanesthetized, the heart exposed, and the LAD ligated.

The rats were euthanized 14 days after coronary occlusion and the hearts harvested, fixed, and sectioned. Myocardial infarction size measured at the level of the mid-papillary heart muscles was scored by Masson's trichrome staining, as previously described, and the images were analyzed in a blinded fashion with ImageJ 1.22 software (NIH Image). Infarction size was expressed as a percentage of the total left ventricular myocardial area.

Intramyocardial Injections of PDGF Induces VEGF and Ang-2

Tissue was assessed in situ to define the growth factor pathways downstream of PDGF in the process of cardioprotection from myocardial infarction cardiac. Young adult F344 rats were anesthetized and underwent left intercostal thoracotomy. The rats received 100 ng of PDGF in 50 μL PBS solution during similar surgery as described above. Control rats received PBS pretreatment. Rats were euthanized 24 hours after injection, and hearts were excised, fixed, and sectioned for immunohistochemistry staining. Rabbit antibodies directed to VEGF (Santa Cruz, #sc-507), angiopoietin-1 and angiopoietin-2 (Ang-2) (Santa Cruz, #sc-8357 and sc-7017) were used as primary antibodies, and visualized with diaminobenzidine (Dako ABC staining kit). Positive vessels numbers were assessed by examining a single mid-papillary section (proximal to the injection site) from each heart and identifying all VEGF or Ang-2 stained endothelial cell-lined structures in a total of 6 high-power fields (magnification×40) per region per heart, as previously described. Edelberg, J. M. et al., Circulation 105, 608-13 (2002).

Pretreatment of Hearts with Downstream Genes

To investigate if the concomitant delivery of PDGF with VEGF and Ang-2 could enhance PDGF cardioprotection, separate sets of rats (n=5) received PDGF, VEGF and Ang-2, or VEGF and Ang-2 (R & D systems, 293-VE and 623-AN), or PDGF alone or PBS control injections 24 hr prior to LAD ligation. Other sets of rats received PDGF, VEGF and Ang-2, or PDGF, or PBS at the time of LAD ligation. All growth factor concentrations were 100 ng in 50 μl of PBS. Rats were sacrificed 14 days post-ligation and hearts harvested, and myocardial necrosis measured as described above.

Concomitant Injection of VEGF and Ang-2 with PDGF-AB at the Time of Ligation

To determine the cardioprotective potential of combination(s) of growth factors injected at the time of myocardial infarction, acute cell death was measured one day following coronary ligation. Sets of rats were injected with combinations of PDGF, VEGF and Ang-2 or with PDGF (N=3, each) at the time of LAD ligation as described above. These rats were sacrificed 24 hours after ligation. Hearts were excised and fixed, sections were prepared for histology.

Heart sections were analyzed for apoptotic induction using TUNEL staining (Roche In situ Cell Death Kit, #684817). Briefly, slides were deparaffinized and rehydrated using histoclear and decreasing grades of alcohol. Sections were then digested in proteinase-K (10 μg/ml)(Roche) solution for 30 minutes at 37° C. The slides were then incubated in mixture of TdT, dNTP and dUDP-TMR for 1 hour at 37° C., and counterstained with DAPI for 5 minutes. Micrographs were taken using both low magnification (4×) and higher magnification field with a fluorescent microscope. Apoptotic cell numbers were counted in 15 fields in each slide.

Masson's trichrome staining of the hearts 14 d post coronary occlusion was performed in order to confirm the expanded window of cardioprotection provided by injection of all three growth factors. Additional sets of rats were injected with PDGF, PDGF with VEGF and Ang-2 (all growth factor concentrations were 100 ng in 50 μl of PBS), and with PBS (N=5, each set) at the time of coronary ligation. Rats were sacrificed 14 days post-ligation and hearts were harvested. Myocardial necrosis was measured as described above.

Statistics

Q-square test was used for assessing survival of the cells. Differences in positive vessels numbers and apoptotic cell numbers were tested by the Student's t test. The extent of myocardial necrosis was compared using Fisher's test. A value of $P<0.05$ was considered significant.

Results

The combination of growth factors PDGF, VEGF and Ang-2, when injected about 2448 hr. prior to myocardial infarction, provides better protection against cardiac tissue damage than does injection of PDGF, VEGF or Ang-2 alone.

Kinetic Window of PDGF-AB Cardioprotection

The kinetic studies of PDGF delivery and myocardial injury were performed to define the therapeutic window of cardioprotection provided by PDGF. Intramyocardial injection of PDGF 24 to 48 hr before LAD ligation reduced the extent of myocardial infarction significantly (FIG. 1). Treatment at times less then 12 hr or greater than 72 hr prior to coronary ligation, however, had no effect on myocardial infarction size, suggesting that genes/pathway induced by PDGF had a narrow temporal window of protection from myocardial injury.

PDGF Pretreatment Induces VEGF and Ang-2

To investigate the actions of genes downstream of PDGF in the cardioprotective pathway, rat cardiac sections pretreated with PDGF were probed for VEGF as well as for Ang-1 and Ang-2.

Immunostaining revealed that PDGF significantly increased the levels of VEGF and Ang-2 (FIG. 2) in the cardiac microvasculature, but did not significantly affect Ang-1 levels (data not shown). Representative sections of VEGF or Ang-2 stained paraffin sections (DAB) were obtained from 4-month old rat hearts that had pretreated with vehicle (PBS) or PDGF 24 h before euthanization. VEGF positive vessels were prominent in PDGF treated sections while there were few positive vessels on PBS treated sections. Similarly, Ang-2 positive vessels were more prevalent in PDGF treated heart sections than in PBS treated section.

Figure 2A:
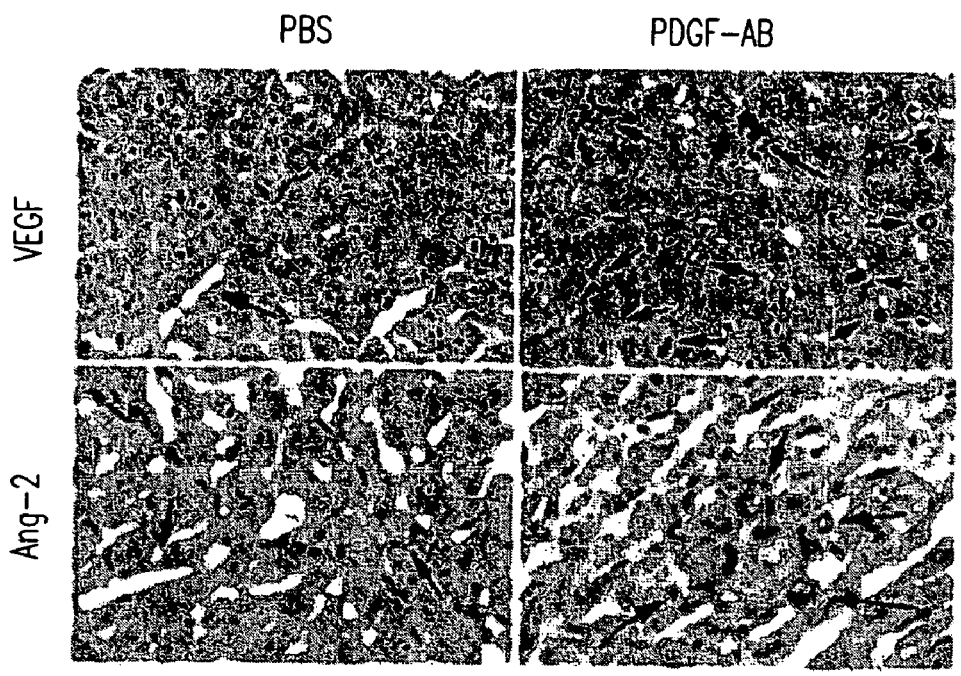
FIG. 2A-B illustrates that PDGF induces both VEGF and Ang-2 in heart tissues.
Figure 2B:
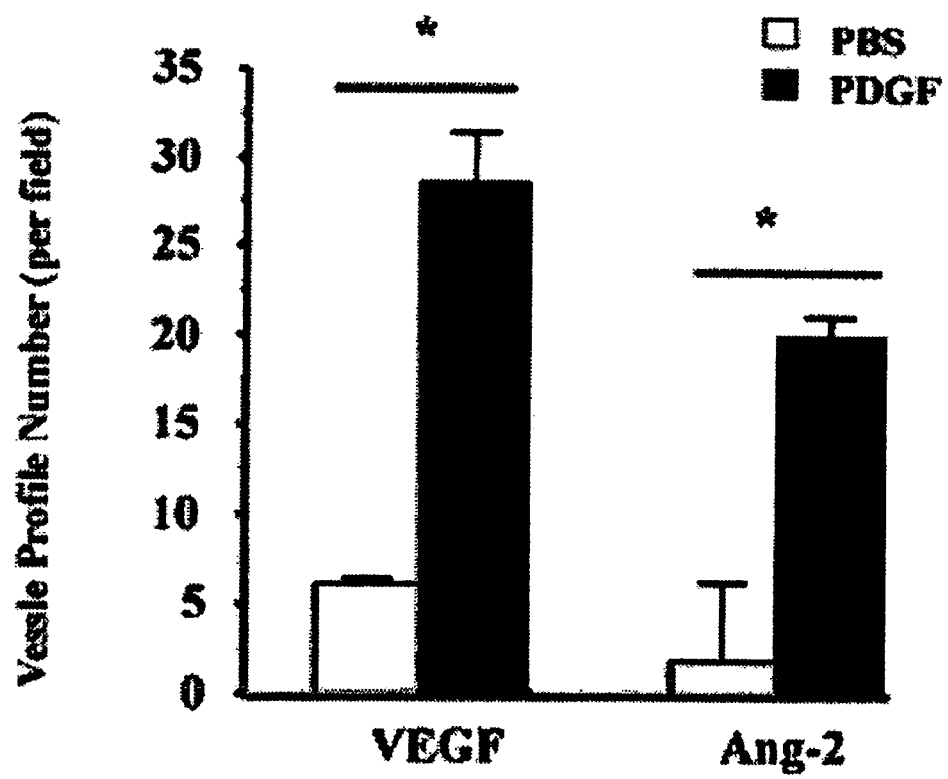

FIG. 2 provides a graph comparing the vessel profile numbers of VEGF or Ang-2 positively stained cells in PDGF or PBS treated hearts sections. As illustrated, there was significant induction of both VEGF and Ang-2 in PDGF treated hearts compared to PBS treated hearts. A P value of $P<0.05$ (*) was observed for PDGF treatment vs. PBS treatment.

Figure 3:
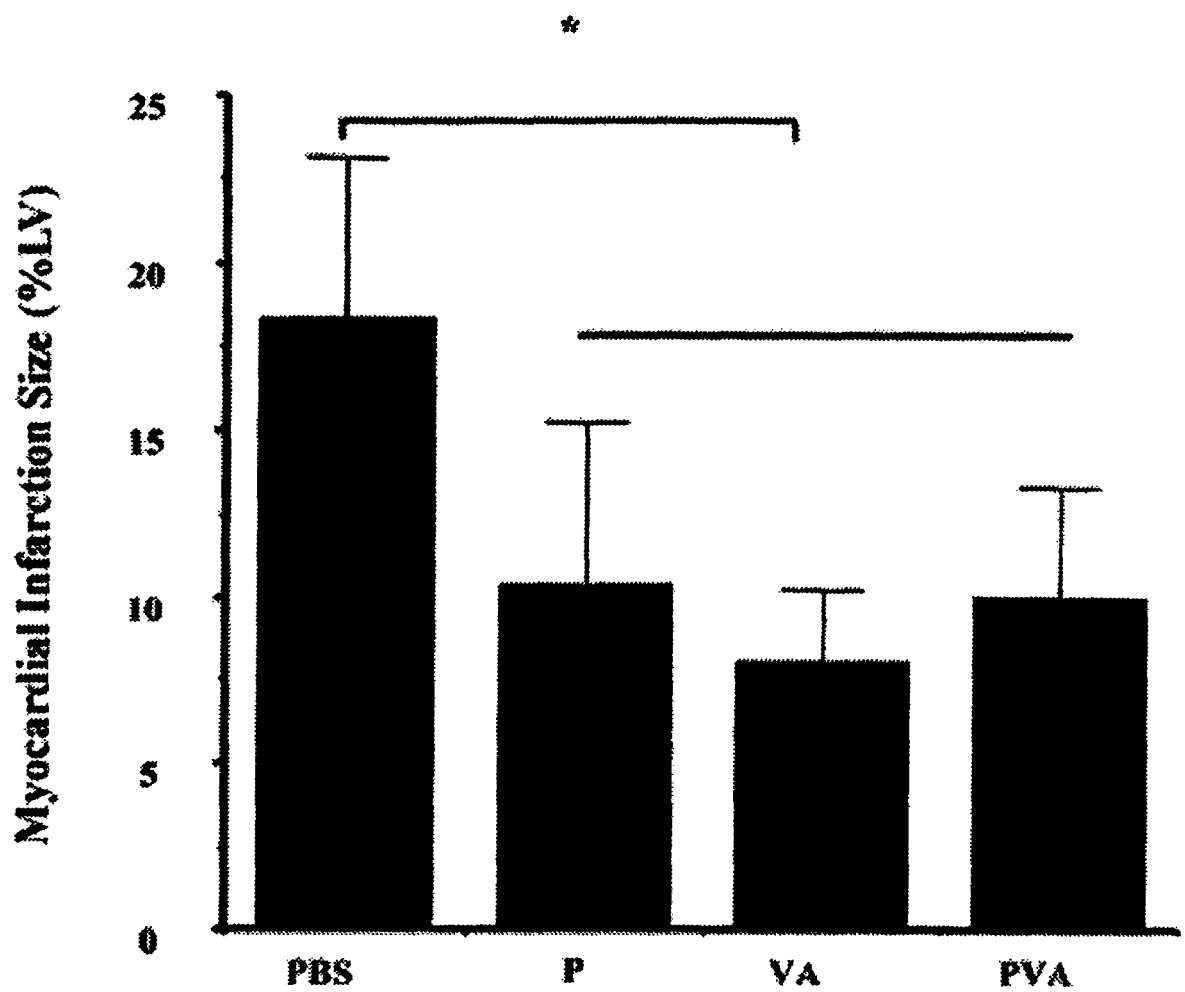
FIG. 3 provides a graph showing the size of the myocardial infarction as assessed by Masson-tricrom staining of rat heart sections. Sections were collected two weeks after pre-injection of PBS, PDGF (P), VEGF and Ang-2 (VA) or PDGF plus VEGF and Ang-2 (PVA). LAD ligation was performed 24 hr after these injections. The infraction area as assessed by blue staining was significantly smaller in VA pretreated heart sections than PBS or PDGF injected sections, PVA did not further reduce infraction size from the extent of PDGF alone. *P<0.05.

The potential cardioprotective function of these factors was then tested by pre-treating hearts with VEGF and Ang-2 together, and in combination with PDGF, prior to coronary occlusion. LAD ligation was performed 24 hr after injection of these factors. Measurements of myocardial necrosis revealed that co-injection of VEGF and Ang-2 provided a similar degree of cardioprotection to that observed with PDGF alone (FIG. 3). While injection of all three factors together was highly beneficial, no further decrease in myocardial infarction size was observed when all three factors were injected together. Hence, the actions of the PDGF pathway factors were not strictly additive when they were administered together 24 hours prior to myocardial infarction. The timing or concentration of factors administered could also have affected the response observed.

Enhanced Cardioprotective Kinetics by Concomitant Delivery of PDGF, VEGF and Ang-2

In order to study the potential synergistic actions of PDGF pathway elements on cardioprotective kinetics, acute myocardial cell death was measured in rat hearts pretreated with different combinations of the three growth factors at the time of coronary occlusion.

Figure 4E:
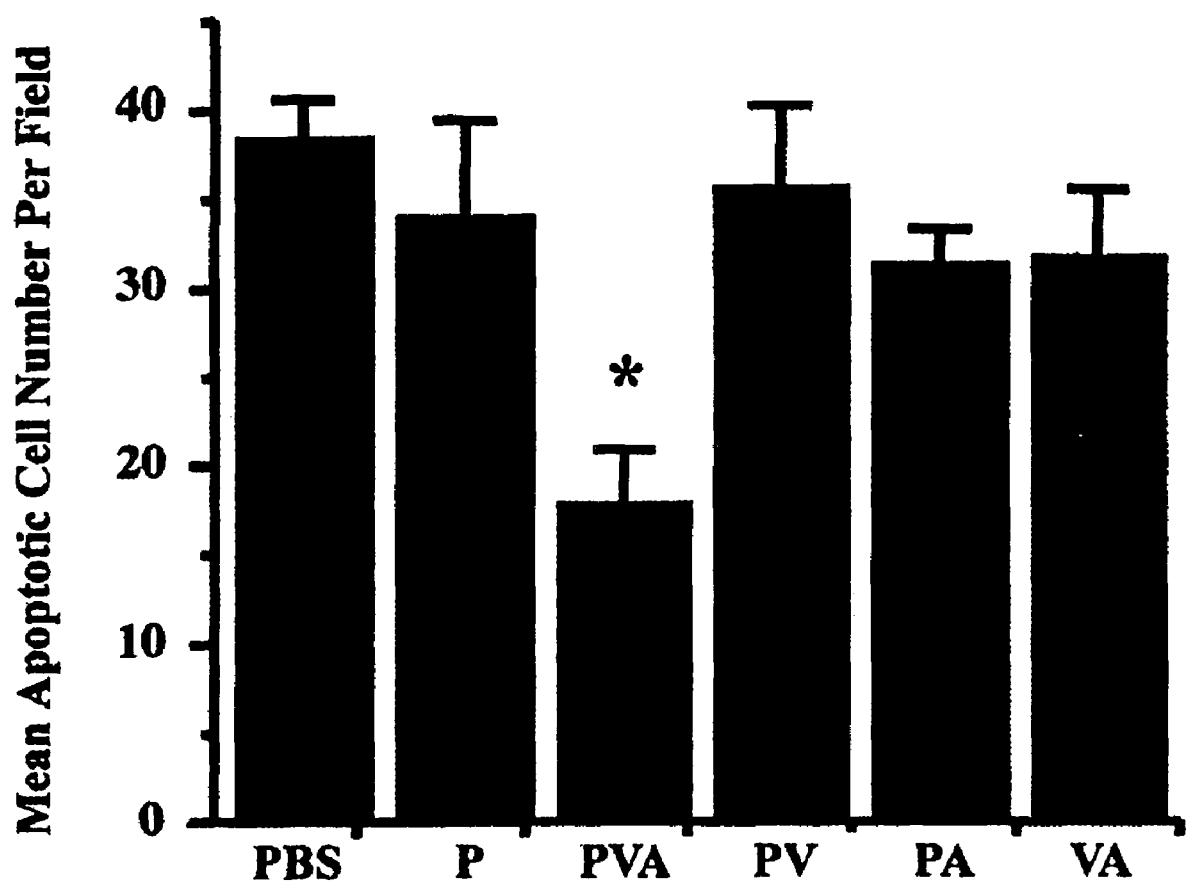

Cardiac TUNEL staining 24 hr after LAD ligation demonstrated that only the triple combination of PDGF, VEGF and Ang-2 limited cardiac cell death, reducing both the area size of apoptotic myocardial tissue and the density of apoptotic cell numbers (FIG. 4). All other combinations failed to achieve such a protective effect. Rats were peri-injected with PBS, or PDGF (P), or PDGF plus VEGF (PV), or PDGF plus Ang-2 (PA), or VEGF plus Ang-2 (VA), or PDGF plus VEGF and Ang-2 (PVA) prior to LAD ligation. Rat heart tissues were then collected 24 hr after LAD ligation, embedded in paraffin, sectioned and TUNEL labeled. It was apparent under low magnification (4×) that apoptotic cells occupied the larger portion of the anterior myocardium in PBS injected heart sections than in the PVA injected heart sections. Under higher magnification (40×) TUNEL positive (red-stained) cell density was significantly higher in PBS injected heart sections than the PVA injected sections (see FIG. 4).

Figure 5A:
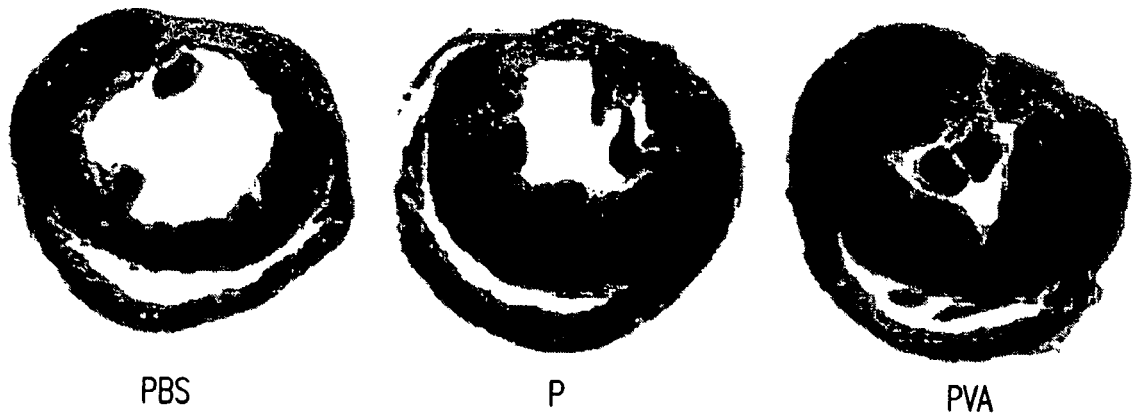
FIG. 5A-B are images (FIG. 5A) and a graph (FIG. 5B) showing the area of the myocardial necrosis (% total of left ventricular myocardium) for rat hearts peri-injected with PBS, PDGF (P) or a combination of PDGF, VEGF and Ang-2 (PVA), prior to LAD 25 ligation. As shown, the combination of PDGF, VEGF and Ang-2 was much more effective at reducing myocardial necrosis than PDGF alone.*P<0.05 PVA vs. all other groups.
Figure 5B:
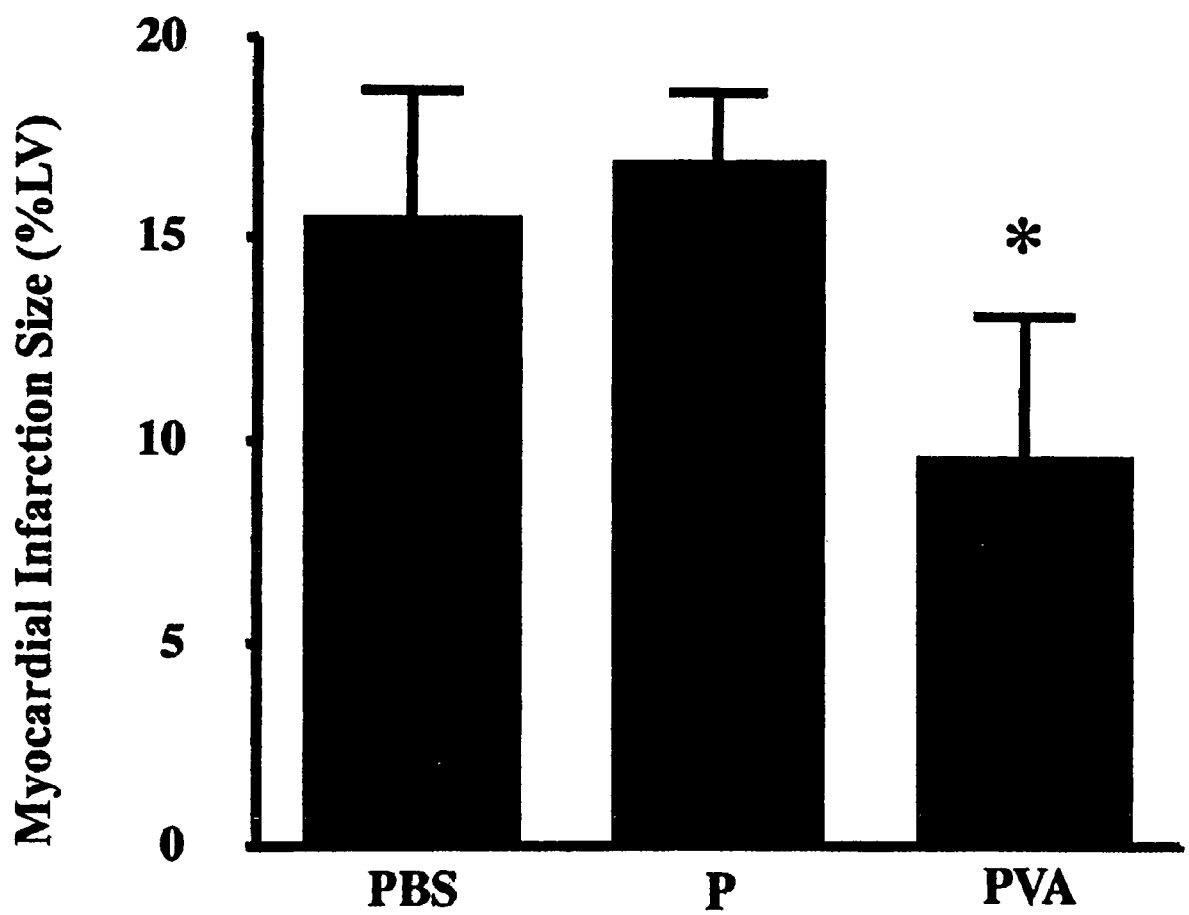

Based on the result of these acute cell death studies, the potential of triple combination peri-injection to decrease myocardial necrosis was assessed. Rats were peri-injected with PBS, PDGF (P), or PDGF plus VEGF and Ang-2 (PVA) prior to LAD ligation (N=5, each). Hearts were collected two weeks after peri-injection, sectioned and stained with Masson's trichrome. Upon examination, it was apparent that the infarction area (stained blue) was significantly smaller in PVA treated heart sections than in PBS or PDGF treated heart sections. These observations are consistent with observations on the area of apoptosis observed and shown in FIG. 4. FIG. 5 provides a graph showing the area of the myocardial necrosis (% total of left ventricular myocardium) for the different peri-injection groups. *P<0.05 PVA vs. all other groups Therefore, delivery of PDGF-AB, VEGF and Ang-2 at the time of coronary occlusion specifically reduced the extent of myocardial infarction size by approximately half compared with hearts treated with control of PDGF alone (FIG. 5).

EXAMPLE 2

Senescent Impairment in the Synergistic Cytokine Pathways that Provide Cardioprotection As shown in the previously by the inventors, pretreatment of rodent hearts with platelet-derived growth factor (PDGF)-AB decreases myocardial injury after coronary occlusion. This Example shows that PDGF-AB cardioprotection is diminished in older animals, suggesting that downstream elements mediating and/or synergizing the actions of PDGF-AB may be limited in aging cardiac vasculature. As shown herein, PDGF-AB induced vascular endothelial growth factor (VEGF) and angiopoietin (Ang)-2 expression in 4-month-old rat cardiac endothelial cells in vitro, but not in 24-month-old heart cells. In vivo injection of young hearts with PDGF-AB increased the densities of VEGF-Flk-1 and Ang-2-Tie-2 positive vessels as well as the PDGF receptor-alpha (PDGFRα). However, in older hearts PDGF-AB-mediated induction was primarily limited to PDGFRα.

Methods

Animals

Studies employing 4- and 24-month-old F344 rats, neonatal and 18-month-old C57BL/6 mice, were performed in compliance with the Institutional Animal Care and Use Committee of Weill Medical College of Cornell University.

Molecular Analysis of Age-Associated PDGF Cytokine Pathways

To define the potential age-associated changes in growth factor pathways downstream of PDGF-AB, cardiac microvascular endothelial cells (CMECs) were isolated from young (4-month-old) and old (24-month-old) rat hearts, as previously described in Cai et al., *Am J Physiol. Heart Circ Physiol* 0.285(2): H463-469 (2003). Cells were treated with PDGF-AB and expression levels of the proangiogenic cytokines VEGF and Ang-2 were assessed by real time reverse transcriptase polymerase chain reaction (RT-PCR).

Briefly, rat hearts were harvested and digested using collagenase (0.2%) and DNase (0.005%) in 10 mL of complete media (DMEM with 110% FCS, endothelial growth supplement (50 μg/mL; Sigma), heparin (30 U/mL), Penicillin (100 U/mL) and Streptomycin (100 μg/mL)) for 45 min at 37° C. Endothelial cells were isolated by incubating the cell suspensions with anti-CD31 coated Dynabeads (Dynal) for 30 min at room temperature, and collected with a magnetic particle collector. Cells were cultured up to 4 passages. Two hours prior to PDGF-AB treatment, the cells were fed with basic media (without serum and endothelial growth supplement), after which PDGF-AB (50 ng/mL, R&D Systems) was added to the wells. Total RNA was isolated at different time points (0, 15 min, 30 min, 1 hr, 3 hr, and 6 hr; n=3 wells per time point) using an Rneasy Mini Kit (Qiagen). cDNA was prepared using Sensisript™ Reverse Transcriptase Kit (Qiagen). Real time PCR was performed using 2 μl of cDNA with SYBR™ Green hot start PCR protocol (AB Biochom) with beta actin levels used as a control (95° C. 600 seconds hot start, denaturation at 95° C. for 30 seconds, annealing at 60° C. for 30 seconds, 72° C. 30 seconds, maximum 40 cycles). The following primer pairs were employed:

```
Beta actin  5'-GTCGTACCACTGGCATTGTG-3'  (SEQ ID NO:13)
                                        (forward);

5'-ACCCTCATAGATGGGCACAG-3'  (SEQ ID NO:14)
                                        (reverse);

Ang-2       5'-TCCGGCGAGGAGTCTAACTA-3'  (SEQ ID NO:15)
                                        (forward);

5'-AGCTGGAAAAGCAGAAGGTG-3'  (SEQ ID NO:16)
                                        (reverse);

VEGF        5'-TGCCTACCTCACCTGTTTCC-3'  (SEQ ID NO:17)
                                        (forward);

5'-TCTGTCTGGCTGTCATCTGG-3'  (SEQ ID NO:18)
                                        (reverse);
```

All experiments were replicated with independent cell isolates.

In Situ Analysis of PDGF Downstream Pathway

To define the in vivo induction of protein patterns of growth factor pathways downstream of PDGF-AB, cardiac tissue was analyzed by immunostaining for VEGF, Ang-1, Ang-2, Flk-1, Flt-1, Tie-1, Tie-2 and PDGFRα. Sets of young adult and old rats were anesthetized and underwent left intercostal thoracotomy and received intramyocardial injections of PDGF-AB or PBS (n=3, per group). After identifying the left anterior descending artery (LAD), PDGF-AB (100 ng/50 μL in PBS) or PBS alone was injected through a 30-gauge needle (two 25 μL injections, 2 mm apart) intro the mid-left ventricular anterior wall. The chest wall was closed, the lungs inflated, the rats were extubated, and the tracheotomy closed. Rats were euthanized 24 hr after injection, and hearts were excised, fixed, and sectioned for immunohistochemistry staining.

Rabbit or goat antibodies directed to VEGF, Ang-1 and Ang-2, Flk-1, Flt-1, Tie-1, Tie-2 and PDGFRα (Santa Cruz Biotechnology) were used as a primary antibodies, and the immunocomplexes were visualized using the ABC staining method (Dako USA, ABC Staining Kit). Positive vessel numbers were assessed in sections at the mid-papillary level of each heart and all stained luminal structures were identified in a total of six high-power fields (40× magnification) per section as previously described. Edelberg et al., *Circulation.* 105(5): 608-613 (2002); Brooks et al., *Science.* 264(5158): 569-571 (1994); Dellian et al., *Am. J. Path.* 149(1): 59-71 (1996).

Senescent Cardiac Allograft Assay

To test the physiological significance of the alterations in aging endothelial function, a cardiac allograft model was employed that allows the assessment of cardiac angiogenic potential in different age groups. Edelberg et al., *Circulation.* 105(5): 608-613 (2002); Edelberg et al., *Circulation Research.* 90(10): E89-93 (2002). In this model, allograft neovascularization is mediated by host endothelial cells, which are recruited into the donor hearts and recapitulate the cardiac myocyte-endothelial cell communication in vivo. See Aird et al., *J. Cell Biol.* 138(5): 1117-1124 (1997).

Briefly, 18-month-old C57BL/6 mice were anaesthetized with avertin (15 μg/mL), and a 10 μL solution containing 0, 1, 3, 10 or 100 ng (n≧20, each group) of PDGB-AB was injected subcutaneously into each ear. C57BL/6 neonatal hearts were transplanted either at the time of PDGF-AB injection, or 24 hr after, via injection into the subcutaneous pinnal tissue on dorsal side of the ear. Allograft viability was scored by pinnal and transplant integrity 1 week after engraftment, as previously described in Edelberg et al., *Circulation.* 105(5): 608-613 (2002); and Edelberg et al., *Circulation Research.* 90(10): E89-93 (2002). Additional sets of senescent hosts were also pretreated with subcutaneous pinnal injections of PDGF-AB (3 ng), VEGF (100 ng), PDGF-AB (3 ng) plus VEGF (100 ng), Ang-2 (100 ng) or PBS alone (n≧20) 24 hr prior to transplantation. Transplantations at the time of injection were also performed by injection of VEGF, PDGF-AB, Ang-2, PDGF-AB plus VEGF (PV), PDGF-AB plus Ang-2 (PA), PDGF-AB plus VEGF plus Ang-2 (PVA) (100 ng of each cytokine), or PBS (n≧10, each group) and then immediate transplantation of C57BL/6 neonatal hearts into the treated sets of ears.

Concomitant Injection of VEGF, Ang-2 and PDGF-AB at the Time of Ligation

To study the potential synergism between PDGF-AB and its downstream growth factors in the intact rat heart, combinations of growth factors were injected intra-myocardially at the time of coronary occlusion. Sets of 4-month-old rats were injected with combinations of PDGF-AB, VEGF and Ang-2 as well as PDGF-AB alone or PBS (100 ng of each in a total of 50 μl of PBS; n=3, per group) as described above, and the left anterior descending (LAD) artery was ligated just below the left atrial appendage with 8-0 nylon sutures. Pallor and regional wall motion abnormality of the left ventricle as well as ST segment elevation confirmed occlusion. These rats were sacrificed 24 hr after ligation.

Hearts from the sacrificed rats were excised and fixed. Heart sections were then analyzed for apoptotic cell death using TUNEL (terminal deoxynucleotidyl transferase-mediated dUTP) staining (Roche In situ Cell Death Kit). Briefly, slides were deparaffinized and rehydrated using histoclear and decreased grades of alcohol. Followed by digestion in proteinase-k (10 μg/mL), slides were incubated in mixture of TdT, dNTP and dUDP-TMR for 1 hr at 37° C., and counterstained with DAPI (InnoGenex). Photomicrographs were taken under both low magnification (4×), and higher magnification (40×) fields using fluorescent microscopy. Apoptotic cell density in the anterior left ventricular wall was then measured in 15 high power fields per heart. The extent of cardiac tissue apoptosis was assessed on reconstructed 4× micrographs using NIH Image J analyzing system and expressed as percentage of left ventricular area.

Additional sets of both 4- and 24-month-old rats received injections of the PDGF-AB, VEGF and Ang-2 combination, PDGF-AB alone, or PBS alone (n>5, each group) at the time of coronary occlusion, as described above. These rats were sacrificed 14 d after ligation and sections at the mid papillary level were stained by Masson's trichrome stain as a measure of the extent of myocardial injury as previously described in Edelberg et al., *Circulation.* 105(5): 608-613 (2002); and Cai et al., *Am J Physiol. Heart Circ Physiol* 0.285(2): H463-469 (2003).

Statistics

Differences in positive vessel numbers and apoptotic cell numbers were tested by the Student's t test. The extent of myocardial infarction was compared using Fisher's test. A value of P<0.05 was considered significant.

Results

Induction of VEGF and Ang-2 by PDGF Pretreatment

Figure 6A:
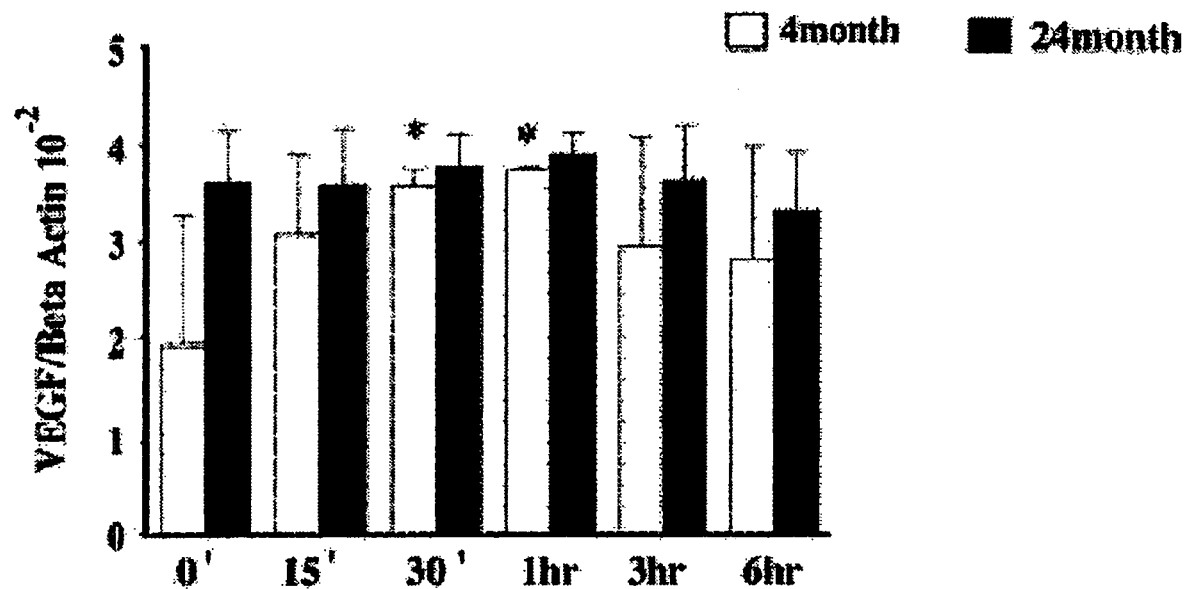
FIGS. 6A-D illustrate that PDGF-AB induces pro-angiogenic cytokines in cardiac microvascular endothelial cells.

Real time RT-PCR revealed that PDGF-AB induced significant increases in the expression of both VEGF and Ang-2 in the young, but not old, rat cardiac microvascular endothelial cells (CMECs) (FIG. 6A). At baseline, however, the older cells expressed higher levels of VEGF, similar to our previous findings with murine CMECs (Edelberg et al., *Circulation.* 105(5): 608-613 (2002)). In response to PDGF-AB, cytokine transcripts in the young CMECs showed an initial rise, which down-regulates late in the time course. The older cells were also responsive to PDGF-AB, however, only with a negative regulation of both VEGF and Ang-2 levels.

Figure 6B:
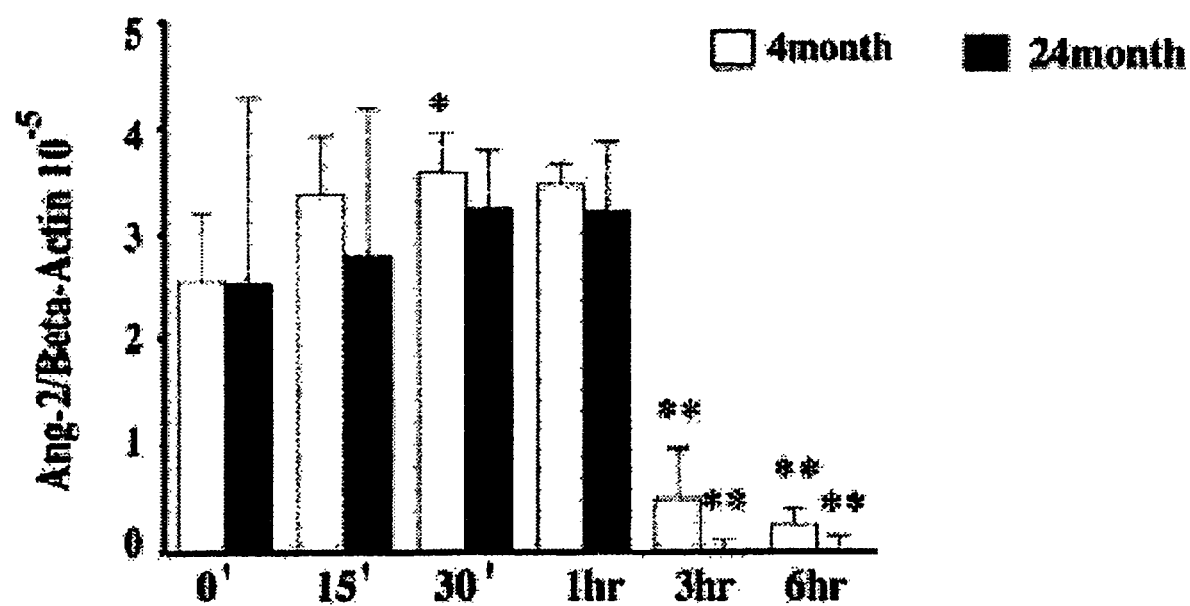
Figure 6C:
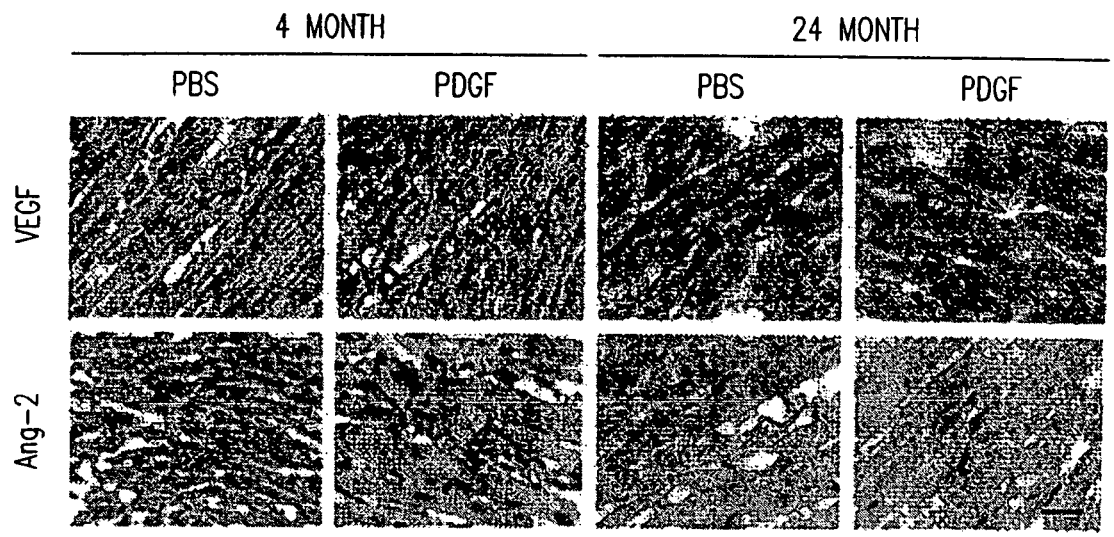
Figure 6D:
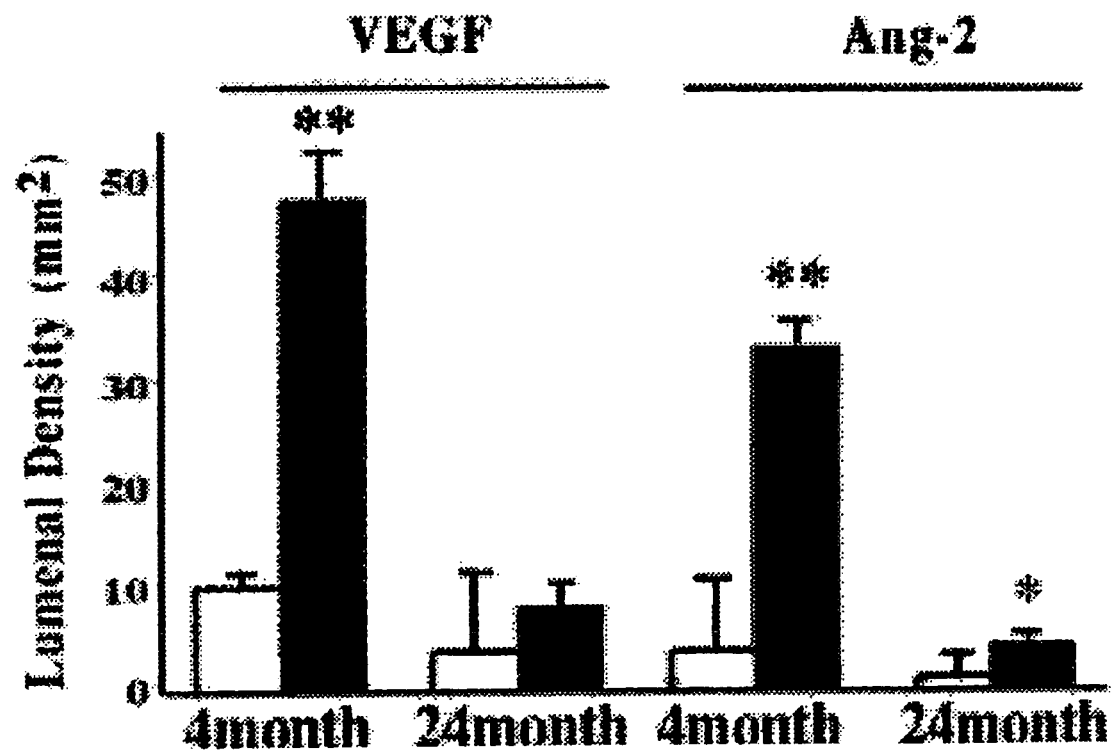

Immunohistology staining revealed in vivo induction of cardiac cytokines by PDGF-AB in the young hearts. Intramyocardial injection of PDGF-AB significantly increased the density of cardiac capillaries stained positive for VEGF and Ang-2 (but not Ang-1, data not shown) in the 4-month-old rat heart sections (FIG. 6B-C). Compared with these young hearts, the density of VEGF and Ang-2 staining was significantly lower in the 24-month-old rat hearts both in the control and PDGF-AB treated sections. Indeed, PDGF-AB injection in the old hearts did not significantly alter VEGF density and resulted in only modest increases in Ang-2 patterns.

Figure 7A:
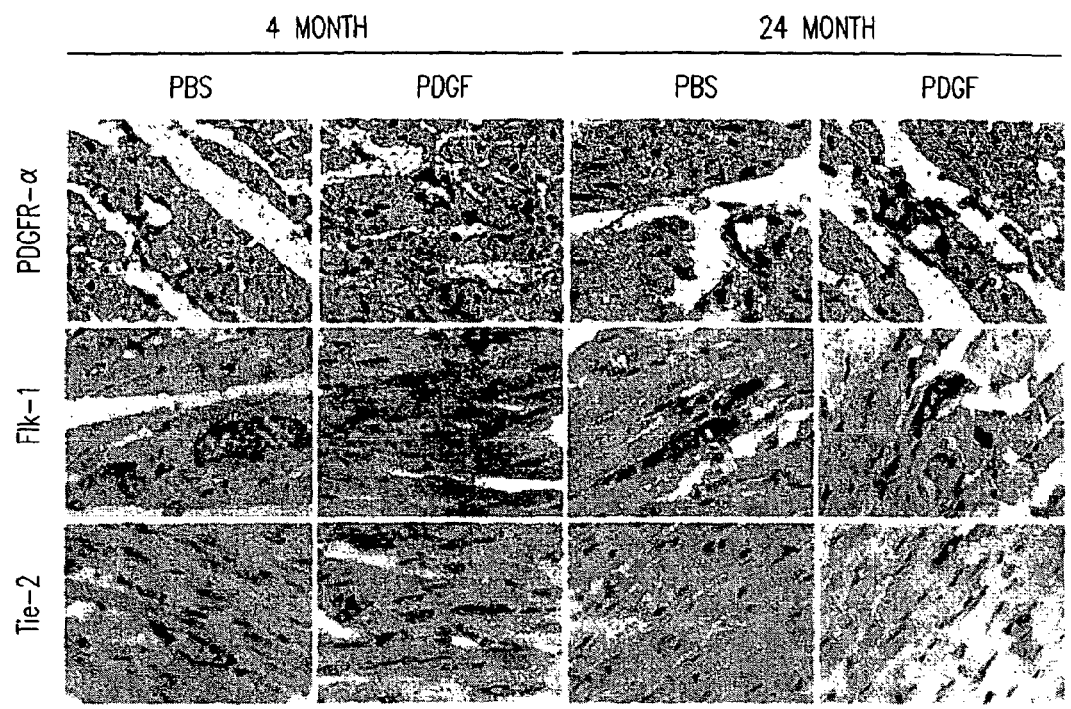
FIGS. 7A-B show that age affects the induction of cytokine receptors by intramyocardial injection of PDGF-AB. VEGF can bind to the flk-1 receptor and Ang-2 is an antagonist of the Tie-2 receptor.
Figure 7B:
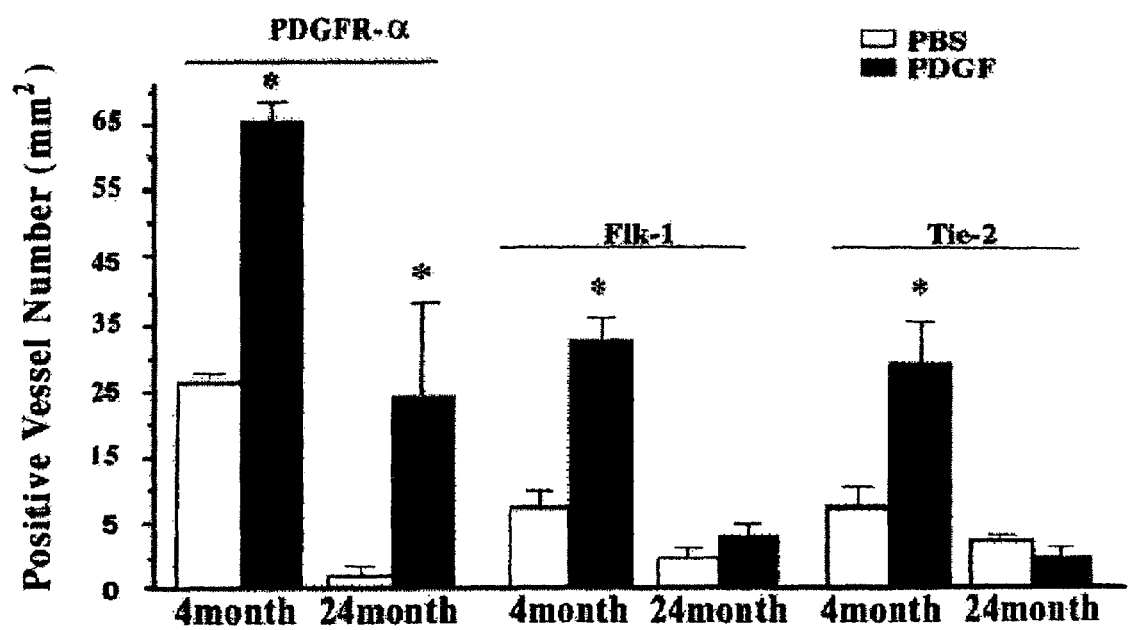

Based on the highly localized staining patterns of VEGF and Ang-2 in the young, but not old hearts, additional experiments were performed to assess potential differences in receptor(s) for these cytokines. Sections of PBS treated rat hearts revealed Flk-1 and Tie-2 staining in the cardiac microvasculature of both age sets (FIG. 7), with approximately two-fold higher levels in the young hearts. PDGFR-α was present in the PBS treated young hearts, but was significantly diminished in the aging control cardiac tissue. PDGF-AB significantly increased the density of all three receptors in the young hearts as well as PDGFR-α in the aging hearts without altering patterning Flk-1 and Tie-2. Immunostaining of Flt-1 and Tie-1 revealed sparse localization in sections of both ages (data not shown).

PDGF Pathway Synergism in Angiogenesis of Exogenous Cardiac Tissue

Figure 8A:
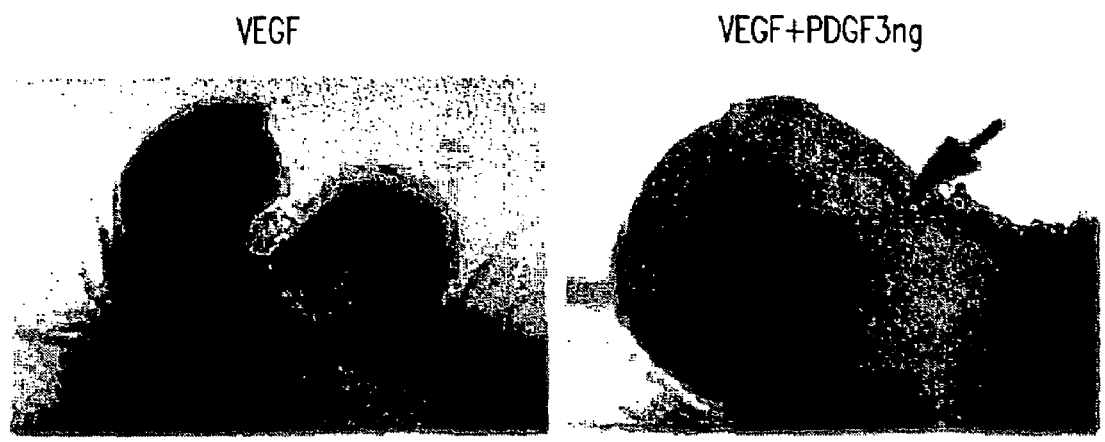
FIGS. 8A-D shows that synergism exists between cytokines active in the restoration of senescent cardiac allografts.
Figure 8B:
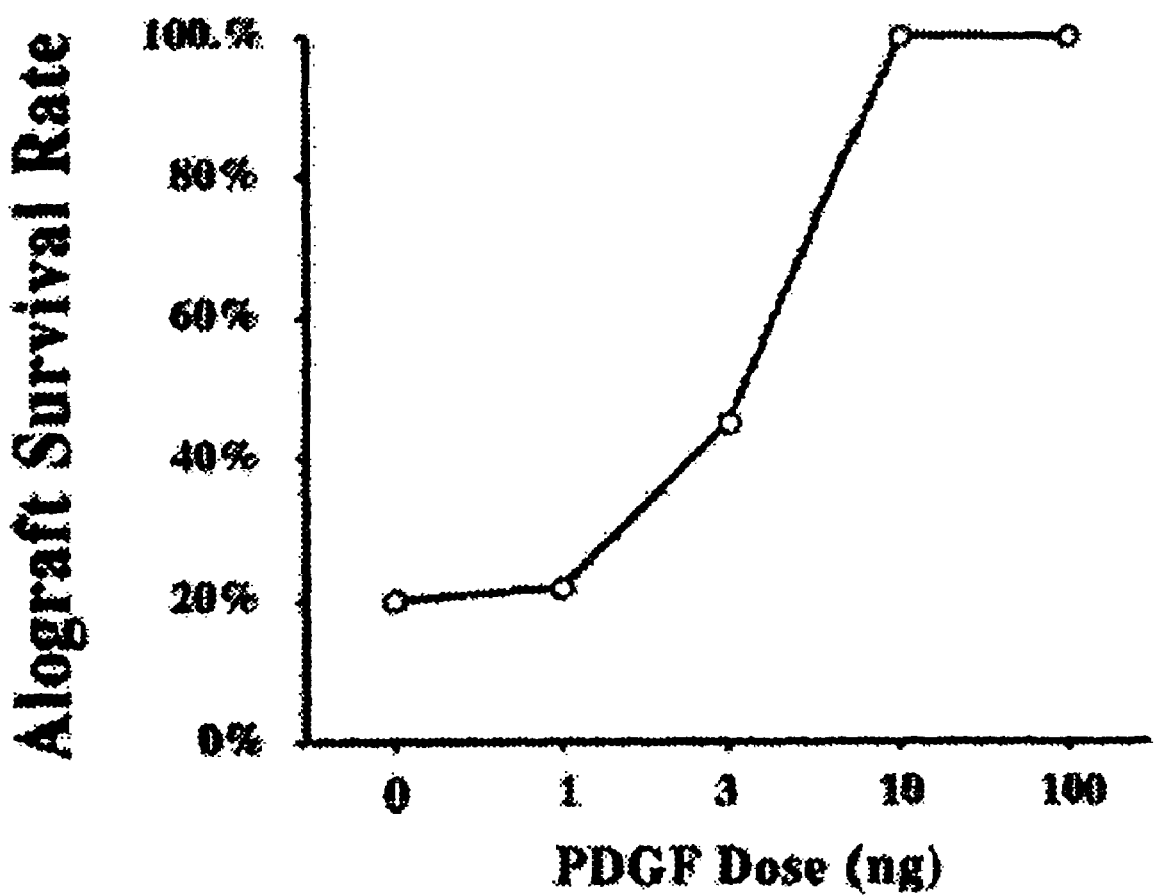
Figure 8C:
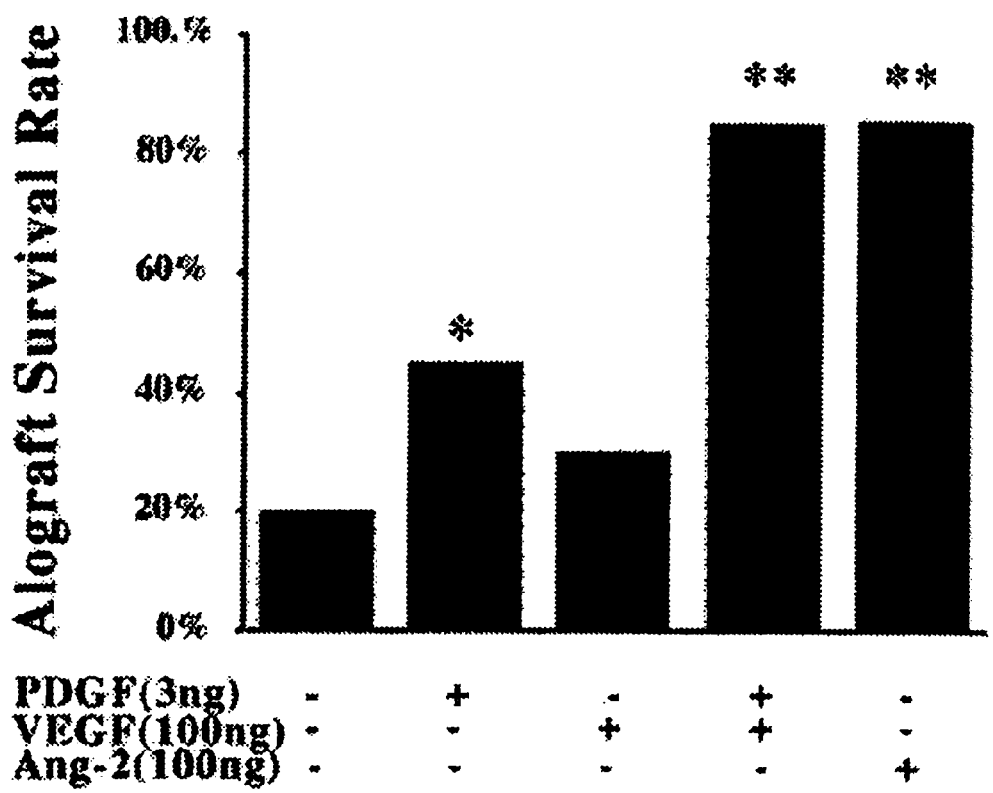

The potential cardiac vascular function of the cytokines in the PDGF-AB pathway was then examined in a senescent cardiac allograft-pinnal transplant pretreatment model. In order to detect synergistic interactions with downstream cytokines, a dose response curve of PDGF-AB restoration of cardiac vascularization was performed. These studies revealed that pinnal treatment the day before transplantation with 3 ng of PDGF-AB rescued approximately half of the cardiac allografts in the aging mice (FIG. 8). While VEGF alone was not sufficient to rescue cardiac viability in this model, the addition of VEGF (100 ng) augmented the actions of the low dose PDGF-AB, fully restoring integrity of the transplanted cardiac allografts (FIGS. 8A-B). Administration of Ang-2 alone was fully effective (FIG. 8C).

Figure 8D:
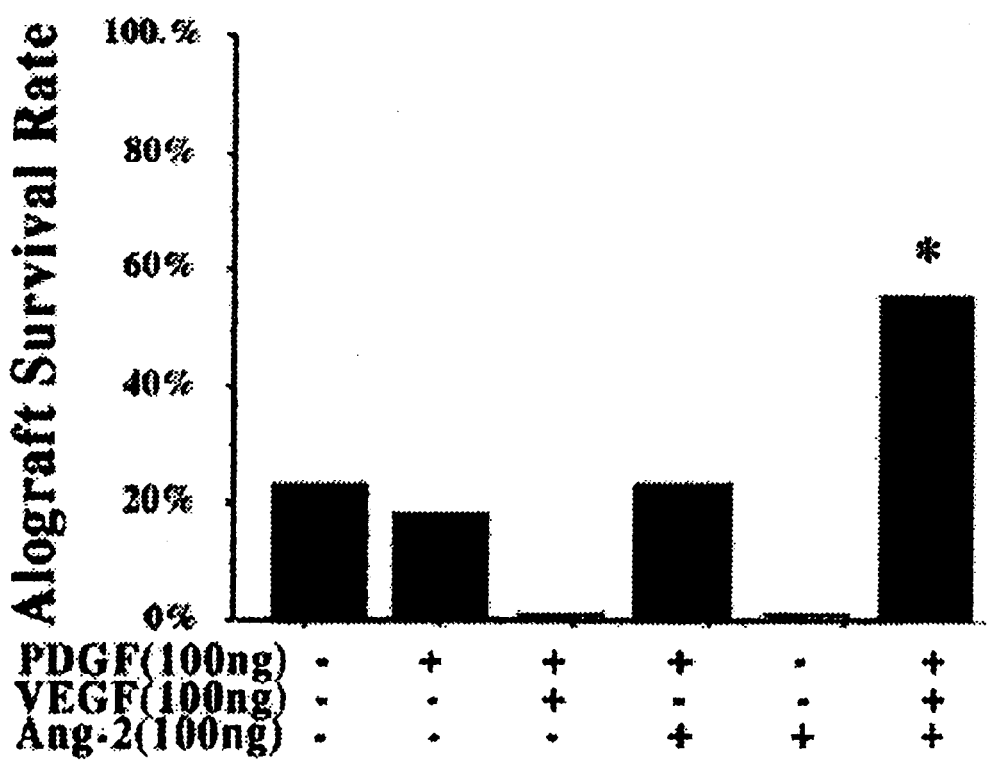

Injection of ears at the time of transplantation with combinations of cytokines demonstrated that the PDGF-AB, VEGF and Ang-2 synergistically augment senescent cardiac allograft viability, shifting the effective temporal window of pinnal treatment (FIG. 8D).

Enhanced Cardioprotective Kinetics by Concomitant Delivery of PDGF, VEGF and Ang-2

The synergistic actions of PDGF-AB pathway cytokines was then confirmed in vivo in an acute myocardial infarction model with delivery of combinations of growth factors at the time of coronary occlusion. Results of cardiac TUNEL staining 24 hr after LAD ligation demonstrated that only the triple combination of PDGF-AB, VEGF and Ang-2 limited cardiac cell death in the young rat heart, reducing both the area and density of myocardial cell apoptosis (FIG. 9).

Figure 10A:
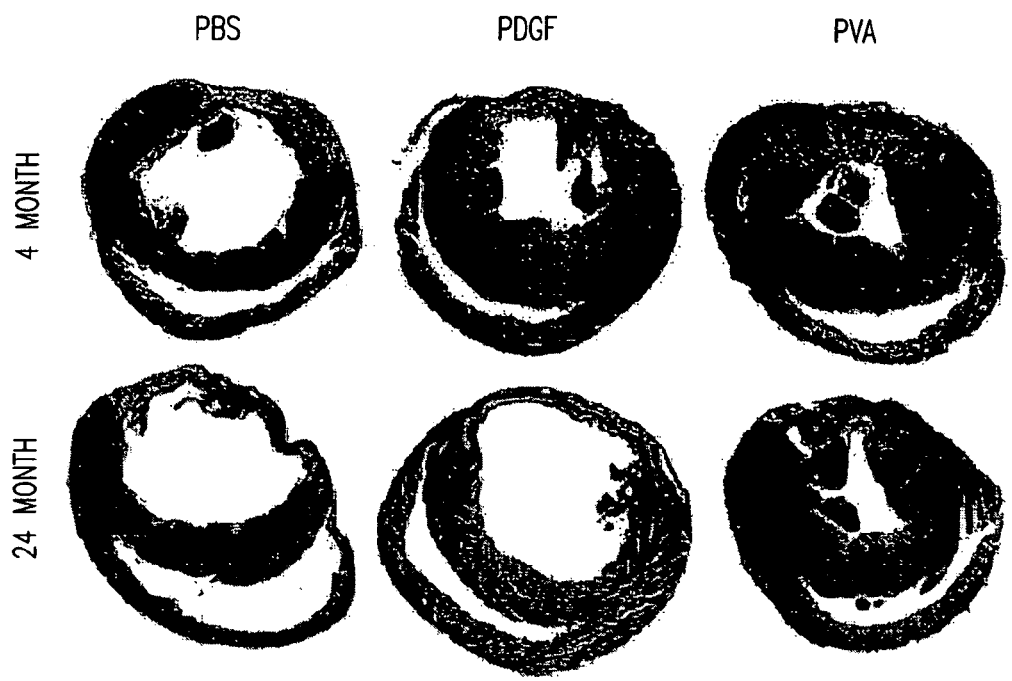
FIG. 10A provides representative Masson's trichrome staining of rat heart sections collected two weeks after peri-injection of PBS, PDGF-AB (P), or PDGF-AB plus VEGF and Ang-2 (PVA) and LAD ligation (n>5, each). Infarction area (blue stain) was significantly smaller in PVA peri-injection heart section than PBS or PDGF-AB injected sections. However, there is significant difference between 4- and 24-months-old rats with PVA treatment.
Figure 10B:
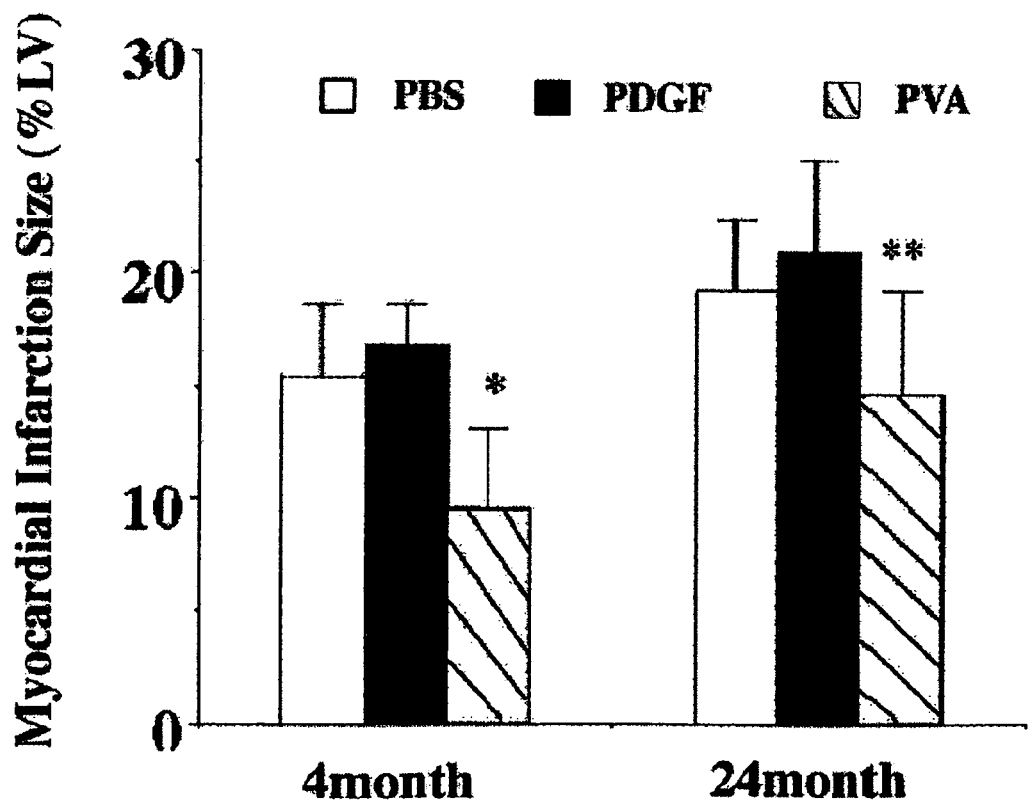
FIG. 10B provides a graph showing the average myocardial infarction size (% left ventricular area). *P<0.05 4-month-old PVA vs. 4-month-old PBS and PDGF-AB and vs. 24-month-old PVA. **P<0.05 24-month-old PVA vs. 24-month-old PBS and PDGF-AB.

Based on the result of these acute cell death studies, the potential of the triple combination delivered peri-ligation was assessed two weeks after myocardial infarction. Indeed, injection of PDGF-AB, VEGF and Ang-2 (PVA) together at the time of coronary occlusion reduced the extent of myocardial infarction in both young and old rat hearts, with greater benefit for the young hearts compared with old hearts, reducing the extent of infarction by 40% and 24%, respectively (FIG. 10).

These studies show that the combination of PDGF-AB, VEGF and Ang-2 provides immediate benefit, at the time of acute coronary occlusion by suppressing cardiac cell death and reducing myocardial injury. While senescent alterations in PDGF-AB-induced pathways are associated with diminished cardioprotective benefit for the aging heart, the aging heart still benefits from administration of a combination of PDGF-AB, VEGF and Ang-2. In particular, after PDGF-AB injection there is a greater than ten-fold increase in PDGFRα cells in the aging heart, suggesting that while the induction of the downstream pathways may have delayed kinetics, such induction is sufficient to provide benefit when delivered at the time of coronary occlusion.

REFERENCES

1. Makino S, Fukuda K, Miyoshi S, et al. Cardiomyocytes can be generated from marrow stromal cells in vitro. *J Clin Invest*. 1999; 103:697-705.
2. Malouf N N, Coleman W B, Grisham J W, et al. Adult-derived stem cells from the liver become myocytes in the heart in vivo. *Am J Pathol*. 2001; 158:1929-35.
3. Orlic D, Kajstura J, Chimenti S, et al. Bone marrow cells regenerate infarcted myocardium. *Nature*. 2001; 410:701-5.
4. Jackson K A, Majka S M, Wang H, et al. Regeneration of ischemic cardiac muscle and vascular endothelium by adult stem cells. *J Clin Invest*. 2001; 107:1395-402.
5. Hakuno D, Fukuda K, Makino S, et al. Bone Marrow-Derived Regenerated Cardiomyocytes (CMG Cells) Express Functional Adrenergic and Muscarinic Receptors. *Circulation*. 2002; 105:380-386.
6. Rafii S, Shapiro F, Pettengell R, et al. Human bone marrow microvascular endothelial cells support long-term proliferation and differentiation of myeloid and megakaryocytic progenitors. *Blood*. 1995; 86:3353-63.
7. Davis T A, Lee K P. Ex vivo expansion of primitive murine hematopoietic progenitor cells on porcine endothelial cells. *Transplant Proc*. 1997; 29:2005.
8. Mohle R, Salemi P, Moore M A, Rafii S. Expression of interleukin-5 by human bone marrow microvascular endothelial cells: implications for the regulation of eosinophilopoiesis in vivo. *Br J Haematol*. 1997; 99:732-8.
9. Rafii S, Mohle R, Shapiro F, et al. Regulation of hematopoiesis by microvascular endothelium. *Leuk Lymphoma*. 1997; 27:375-86.
10. Yourey P A, Gohari S, Su J L, Alderson R F. Vascular endothelial cell growth factors promote the in vitro development of rat photoreceptor cells. *J Neurosci*. 2000; 20:6781-8.
11. Palmer T D, Willhoite A R, Gage F H. Vascular niche for adult hippocampal neurogenesis. *J Comp Neurol*. 2000; 425:479-94.
12. Wang T, FitzGerald T J, Haregewoin A. Differential expression of nitric oxide synthases in EGF-responsive mouse neural precursor cells. *Cell Tissue Res*. 1999; 296: 489-97.
13. Edelberg J M, Tang L, Hattori K, et al. Young Adult Bone Marrow-Derived Endothelial Precursor Cells Restore Aging-Impaired Cardiac Angiogenic Function. *Circ. Res*. 2002; 90:e89-e93.
14. Edelberg J M, Aird W C, Wu W, et al. PDGF mediates cardiac microvascular communication. *J Clin Invest*. 1998; 102:837-43.
15. Edelberg J M, Lee S H, Kaur M, et al. Platelet-Derived Growth Factor-AB Limits the Extent of Myocardial Infarction in a Rat Model: Feasibility of Restoring Impaired Angiogenic Capacity in the Aging Heart. *Circulation*. 2002; 105:608-613.
16. Weinsaft J W, Edelberg J M. Aging-Associated Changes in Vascular Activity—A Potential Link to Geriatric Cardiovascular Disease. *Amer J Geriatric Cardiology*. 2001; 10:348-354.

17. Edelberg J M, Jacobson J T, Gidseg D S, et al. Enhanced myocyte-based biosensing of the blood-borne signals regulating chronotropy. *J Appl Physiol.* 2002; 92:581-5.
18. Christini D J, Walden J, Edelberg J M. Direct biologically-based biosensing of dynamic physiological Function. *Amer J Physiol.* 2001; 280:H2006-2010.
19. Betsholtz C. Role of platelet-derived growth factors in mouse development. *Int J Dev Biol.* 1995; 39:817-25.
20. Ataliotis P, Mercola M. Distribution and functions of platelet-derived growth factors and their receptors during embryogenesis. *Int Rev Cytol.* 1997; 172:95-127.
21. Cheng, W. et al. Programmed myocyte cell death affects the viable myocardium after infarction in rats. *Exp Cell Res* 226, 316-27 (1996).
22. Xue, L. & Greisler, H. P. Angiogenic effect of fibroblast growth factor-1 and vascular endothelial growth factor and their synergism in a novel in vitro quantitative fibrin-based 3-dimensional angiogenesis system. *Surgery* 132, 259-67 (2002).
23. Yoshiji, H. et al. Synergistic effect of basic fibroblast growth factor and vascular endothelial growth factor in murine hepatocellular carcinoma. *Hepatology* 35, 834-42 (2002).
24. Katada, J. et al. Significance of vascular endothelial cell growth factor up-regulation mediated via a chymase-angiotensin-dependent pathway during angiogenesis in hamster sponge granulomas. *J Pharmacol Exp Ther* 302, 949-56 (2002).
25. Ray, P. S., Estrada-Hemandez, T., Sasaki, H., Zhu, L. & Maulik, N. Early effects of hypoxia/reoxygenation on VEGF, ang-1, ang-2 and their receptors in the rat myocardium: implications for myocardial angiogenesis. *Mol Cell Biochem* 213, 145-53 (2000).
26. Richardson, T. P., Peters, M. C., Ennett, A. B. & Mooney, D. J. Polymeric system for dual growth factor delivery. *Nat Biotechnol* 19, 1029-34 (2001).
27. Patan, S. Vasculogenesis and angiogenesis as mechanisms of vascular network formation, growth and remodeling. *J Neurooncol* 50, 1-15 (2000).
28. Breier, G. Functions of the VEGF/VEGF receptor system in the vascular system. *Semin Thromb Hemost* 26, 553-9 (2000).
29. Liu, W. et al. Antiangiogenic therapy targeting factors that enhance endothelial cell survival. *Semin Oncol* 29, 96-103 (2002).
30. Reinmuth, N. et al. Induction of VEGF in perivascular cells defines a potential paracrine mechanism for endothelial cell survival. *Faseb J* 15, 1239-41 (2001).
31. Kim, I. et al. Angiopoietin-2 at high concentration can enhance endothelial cell survival through the phosphatidylinositol 3'-kinase/Akt signal transduction pathway. *Oncogene* 19, 4549-52 (2000).
32. Holash, J. et al. Vessel cooption, regression, and growth in tumors mediated by angiopoietins and VEGF. *Science* 284, 1994-8 (1999).
33. Blanc-Brude, O. P. et al. Inhibitor of apoptosis protein survivin regulates vascular injury. *Nat Med* 8, 987-94 (2002).
34. Umansky, S. R. & Tomei, L. D. Apoptosis in the heart. *Adv Pharmacol* 41, 383-407 (1997).
35. Gottlieb, R. A. & Engler, R. L. Apoptosis in myocardial ischemia-reperfusion. *Ann NY Acad Sci* 874, 412-26 (1999).
36. Hinescu, M. E. Cardiac apoptosis: from organ failure to allograft rejection. *J Cell Mol Med* 5, 143-52 (2001).
37. Tomei, L. D. & Umansky, S. R. Apoptosis and the heart: a brief review. *Ann NY Acad Sci* 946, 160-8 (2001).
38. Guttenplan, N., Lee, C. & Frishman, W. H. Inhibition of myocardial apoptosis as a therapeutic target in cardiovascular disease prevention: focus on caspase inhibition. *Heart Dis* 3, 313-8 (2001).
39. Zou, Z., Sasaguri, S., Rajesh, K. G. & Suzuki, R. dl-3-Hydroxybutyrate administration prevents myocardial damage after coronary occlusion in rat hearts. *Am J Physiol Heart Circ Physiol* 283, H1968-74 (2002).
40. Kovacs, P. et al. Non-specific caspase inhibition reduces infarct size and improves post-ischaemic recovery in isolated ischaemic/reperfused rat hearts. *Naunyn Schmiedebergs Arch Pharmacol* 364, 501-7 (2001).

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims.

As used herein and in the appended claims, the singular forms "a," "an," and "the" include plural reference unless the context clearly dictates otherwise. Thus, for example, a reference to "an antibody" includes a plurality (for example, a solution of antibodies or a series of antibody preparations) of such antibodies, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

What is claimed:

1. A method of increasing survival of blood vessels by reducing apoptosis of blood vessel cells during or after vascular injury in a patient consisting of administering to the patient a therapeutically effective amount of platelet derived growth factor, angiopoietin-2, and vascular endothelial growth factor, and thereby increasing survival of blood vessels by reducing apoptosis of blood vessel cells in the patient during or after vascular injury.

2. The method of claim 1, wherein the platelet derived growth factor, angiopoietin-2, and vascular endothelial growth factor are administered together in combination with a pharmaceutically acceptable carrier.

3. The method of claim 1, wherein the vascular injury comprises occlusion of an artery.

4. The method of claim 1, increasing survival of blood vessels comprises preventing blood vessel injury after vascular occlusion.

5. The method of claim 1, wherein the blood vessels are cardiac blood vessels.

6. The method of claim 1, wherein the administration is by intravascular, intravenous, intraarterial, intraperitoneal, intraventricular infusion, stent, infusion catheter, balloon catheter, bolus injection, direct application to tissue surfaces during surgery, or topical administration.

7. The method of claim 1, wherein administration is directly into a Patient's heart or vasculature.

8. The method of claim 1, wherein platelet derived growth factor is platelet derived growth factor AB, platelet derived growth factor A, platelet derived growth factor B, or a mixture thereof.

9. The method of claim 1, wherein the platelet derived growth factor comprises SEQ ID NO:1, SEQ ID NO:2, SEQ ID NO:3, SEQ ID NO:4, SEQ ID NO:5, SEQ ID NO:6 or a mixture thereof.

10. The method of claim 1, wherein the angiopoietin-2 comprises SEQ ID NO:7, SEQ ID NO:8, or a mixture thereof.

11. The method of claim 1, wherein the vascular endothelial growth factor comprises SEQ ID NO:9, SEQ ID NO:10, SEQ ID NO:11, SEQ ID NO:12, or a mixture thereof.

12. A method of reducing myocardial necrosis in a patient consisting of administering to the patient a therapeutically effective amount of platelet derived growth factor, angiopoietin-2, and vascular endothelial growth factor during or just after myocardial infarction, thereby reducing myocardial necrosis in the patient.

13. The method of claim 12, wherein the platelet derived growth factor, angiopoietin-2, and vascular endothelial growth factor are administered together in combination with a pharmaceutically acceptable carrier.

14. The method of claim 12, wherein the administration is by intravascular, intravenous, intraarterial, intraperitoneal, intraventricular infusion, stent, infusion catheter, balloon catheter, bolus injection, direct application to tissue surfaces during surgery, or topical administration.

15. The method of claim 12, wherein the administration is parenteral.

16. The method of claim 12, wherein administration is directly into a heart or into cardiac vasculature of the patient.

17. The method of claim 12, wherein platelet derived growth factor is platelet derived growth factor AB, platelet derived growth factor A, platelet derived growth factor B, or a mixture thereof.

18. The method of claim 12, wherein the platelet derived growth factor comprises SEQ ID NO:1, SEQ ID NO:2, SEQ ID NO:3, SEQ ID NO:4, SEQ ID NO:5, SEQ ID NO:6 or a mixture thereof.

19. The method of claim 12, wherein the angiopoietin-2 comprises SEQ ID NO:7, SEQ ID NO:8, or a mixture thereof.

20. The method of claim 12, wherein the vascular endothelial growth factor comprises SEQ ID NO:9, SEQ ID NO:10, SEQ ID NO:11, SEQ ID NO:12, or a mixture thereof.

21. The method of claim 12, wherein the platelet derived growth factor, angiopoietin-2, and vascular endothelial growth factor are administered before myocardial infarction.

22. The method of claim 12, wherein the platelet derived growth factor, angiopoietin-2, and vascular endothelial growth factor are administered during or just after myocardial infarction.

23. A method of improving survival of transplanted tissue in a patient consisting of administering to the patient a therapeutically effective amount of platelet derived growth factor, angiopoietin-2, and vascular endothelial growth factor to thereby improve the survival of transplanted tissue in the patient.

24. The method of claim 23, wherein the platelet derived growth factor, angiopoietin-2, and vascular endothelial growth factor are administered in combination.

25. The method of claim 23, wherein the platelet derived growth factor, angiopoietin-2, and vascular endothelial growth factor are administered in combination at the site of the transplant.

26. The method of claim 23, wherein administering is continued after transplantation.

27. The method of claim 23, wherein improving survival of transplanted tissue comprises decreasing apoptosis of transplanted tissues.

28. The method of claim 23, wherein the transplanted tissues are vascular or heart tissues.

29. The method of claim 23, wherein platelet derived growth factor is platelet derived growth factor AB, platelet derived growth factor A, platelet derived growth factor B, or a mixture thereof.

30. The method of claim 23, wherein the platelet derived growth factor comprises SEQ ID NO:1, SEQ ID NO:2, SEQ ID NO:3, SEQ ID NO:4, SEQ ID NO:5, SEQ ID NO:6 or a mixture thereof.

31. The method of claim 23, wherein the angiopoietin-2 comprises SEQ ID NO:7, SEQ ID NO:8, or a mixture thereof.

32. The method of claim 23, wherein the vascular endothelial growth factor comprises SEQ ID NO:9, SEQ ID NO:10, SEQ ID NO:11, SEQ ID NO:12, or a mixture thereof.

\* \* \* \* \*